US010955502B2

(12) United States Patent
Traverso et al.

(10) Patent No.: US 10,955,502 B2
(45) Date of Patent: Mar. 23, 2021

(54) MRI APPARATUS CONTROL SYSTEM, A USER INTERFACE FOR MANAGING THE SAID CONTROL SYSTEM AND AN MRI SYSTEM COMPRISING THE SAID CONTROL SYSTEM AND THE SAID USER INTERFACE

(71) Applicant: Esaote S.p.A., Genoa (IT)

(72) Inventors: Paolo Traverso, Genoa (IT); Amedeo Buonanno, Sant'arpino (IT)

(73) Assignee: Esaote S.p.A., Genoa (IT)

( * ) Notice: Subject to any disclaimer, the term of this patent is extended or adjusted under 35 U.S.C. 154(b) by 0 days.

(21) Appl. No.: 16/194,579

(22) Filed: Nov. 19, 2018

(65) Prior Publication Data
US 2019/0154780 A1 May 23, 2019

(30) Foreign Application Priority Data
Nov. 23, 2017 (EP) .................................... 17203344

(51) Int. Cl.
  G06F 3/048 (2013.01)
  G01R 33/54 (2006.01)
  G06F 3/0483 (2013.01)
  G06F 3/0482 (2013.01)
  G06F 16/16 (2019.01)
  G16H 40/63 (2018.01)
  (Continued)

(52) U.S. Cl.
  CPC ......... *G01R 33/546* (2013.01); *G06F 3/0482* (2013.01); *G06F 3/0483* (2013.01); *G06F 16/168* (2019.01); *G16H 10/60* (2018.01); *G16H 40/63* (2018.01); *A61B 5/055* (2013.01); *A61B 5/7475* (2013.01)

(58) Field of Classification Search
  None
  See application file for complete search history.

(56) References Cited

U.S. PATENT DOCUMENTS 6,353,445 B1 3/2002 Babula et al.
6,904,161 B1 6/2005 Becker et al.
(Continued)

FOREIGN PATENT DOCUMENTS

EP        1315115 A2    5/2003

OTHER PUBLICATIONS

Search Report dated May 14, 2018, by the European Patent Office for Application No. 17203344.1.
(Continued)

*Primary Examiner* — William C Trapanese
(74) *Attorney, Agent, or Firm* — Buchanan Ingersoll & Rooney PC

(57) ABSTRACT

An MRI control system with a user interface which is windows inspired by including toolbars at the upper side of the window, providing active labels related to specific examinations or classes of tasks, each label opening specific windows related to the task again provided with toolbars, active buttons and menus. According to a further aspect the control system is configured for providing a dynamic interaction between the records in a database relating to single cases of the same patient or of different patient, which allows to address the record of a database to which a visualized image or data report belongs by simply clicking on the image or report or by visualizing the said image or report.

21 Claims, 44 Drawing Sheets

(51) Int. Cl.
  *G16H 10/60* (2018.01)
  *A61B 5/00* (2006.01)
  *A61B 5/055* (2006.01)

(56) References Cited

U.S. PATENT DOCUMENTS

| | | | |
|---|---|---|---|
| 2003/0196167 A1* | 10/2003 | Dewar | G06Q 10/04 |
| | | | 715/223 |
| 2007/0055135 A1 | 3/2007 | Benschop et al. | |
| 2011/0286647 A1* | 11/2011 | Cao | G06F 16/54 |
| | | | 382/131 |
| 2012/0323113 A1* | 12/2012 | Biber | G01R 33/3875 |
| | | | 600/422 |
| 2015/0277670 A1* | 10/2015 | Louch | G06F 3/0482 |
| | | | 715/794 |
| 2016/0292176 A1* | 10/2016 | Resnick | G06F 16/13 |
| 2016/0356872 A1 | 12/2016 | Zhao et al. | |
| 2016/0358326 A1* | 12/2016 | Sarachan | G06F 19/321 |

OTHER PUBLICATIONS

Tomovision: "sliceOmatic User's Manual Version 4.3", Aug. 2011, pp. 1-288, Retrieved from the Internet: https://www.tomovision.com/download/binaries/sliceO43.pdf.

Utku, et al., "Improved computerized evaluation of abdominal aortic aneurysm", Turk J Elec Eng & Comp Sci, Jan. 2012, pp. 1408-1424, vol. 20, No.Sup.2, http://journals.tubitak.gov.tr/elektrik/issues/elk-12-20-sup.2/elk-20-sup.2-14-1008-668.pdf.

* cited by examiner

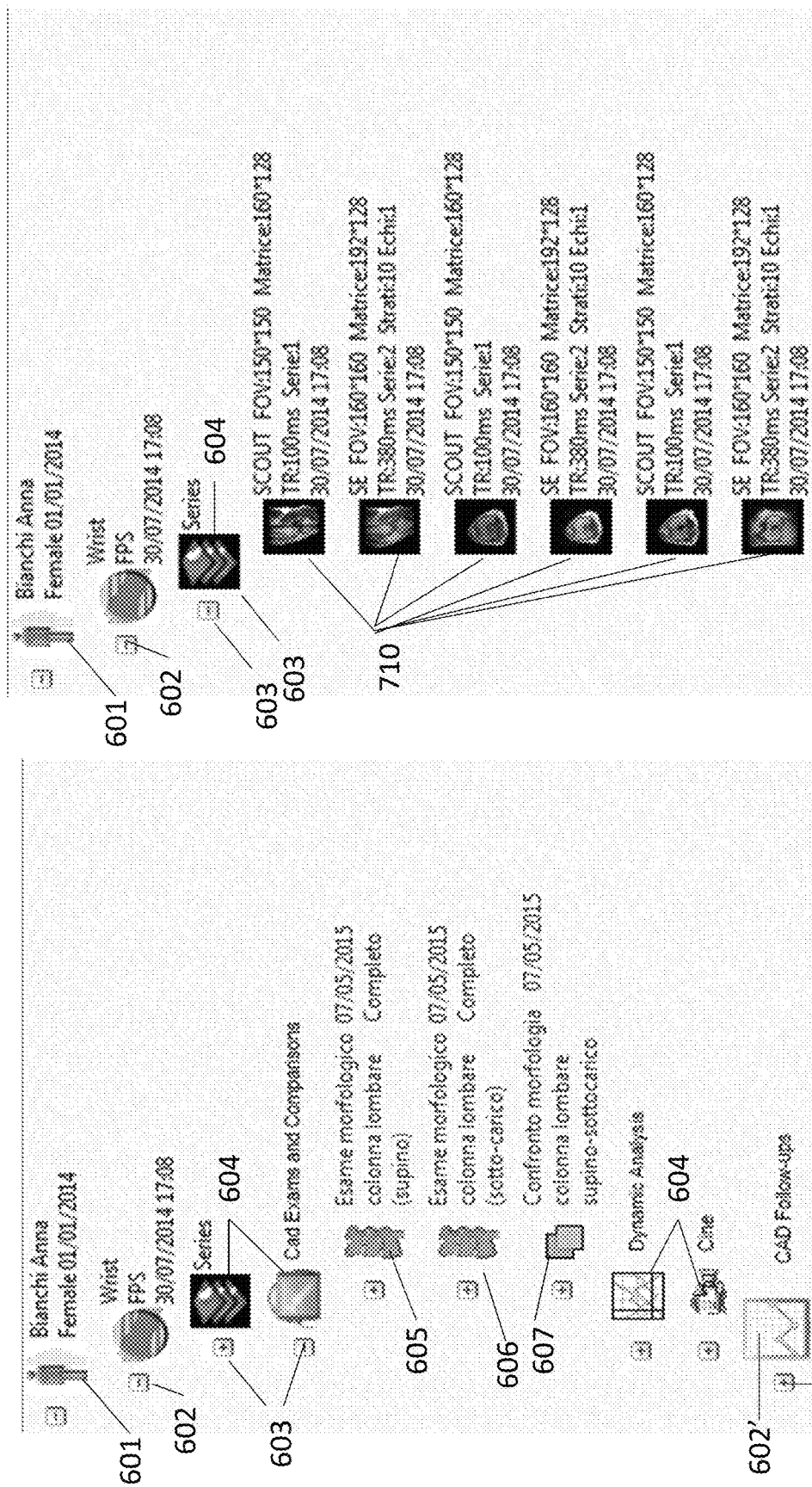

1901
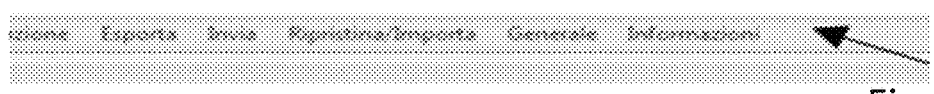
Fig. 19B 1903                    1913

1900

MRI APPARATUS CONTROL SYSTEM, A USER INTERFACE FOR MANAGING THE SAID CONTROL SYSTEM AND AN MRI SYSTEM COMPRISING THE SAID CONTROL SYSTEM AND THE SAID USER INTERFACE

BACKGROUND OF THE INVENTION

The invention relates to an MRI apparatus control system, a user interface for managing the said control system and an MRI system comprising the said control system and the said user interface.

Current MRI imaging systems are provided with control systems which are computer implemented devices allowing to manage the settings of the scanner for carrying out the image acquisition process, the image reconstruction process extracting image data from the received signals and reconstructing an image or a sequence of images from the image data, processing the image data and/or the image or images in order to extract information, store the acquired image or images by univocally correlating the images to a patient and or to other data, such as for example a pathology related to the acquired image or images, manage the patient database and other activities such as for example manage a database of scanning protocols, image reconstruction protocols and or image processing protocols.

US2007055135 discloses a diagnostic imaging system, in particular a magnetic resonance imaging system with a user interface. The diagnostic imaging system comprises a control system to control the execution of operational items by the diagnostic imaging system. A user interface is coupled to the control system, the user interface including a scheduler module which forms an ordered selection of operational items. The operational items are executed on the basis of the ordered selection. The ordered selection concerns the order, timing and conditions to be fulfilled to execute the operational items. The control system and the user interface are limited to merely input the settings of the MRI scanner for acquiring an image and for managing the workflow of the image acquisition and reconstruction steps.

Another example of control system for an MRI imaging system is disclosed in U.S. Pat. No. 6,353,445B1. This document discloses a user interface for interactively exchanging service data between medical diagnostic systems and remote field service facilities. The interface provides a series of user-viewable pages for the display and input of service requests, service reports, messages, protocols. The user interface may further include on-screen input devices, such as graphical buttons, for executing service requests, accessing service messages and reports. The image processing engine cannot be accessed directly by the user of the MRI system, nor the user of the MRI system is able to govern or influence the image processing or CAD processes applied to the image data or to the image.

Document U.S. Pat. No. 6,904,161B1 discloses a computer-implemented method and apparatus for workflow configuration and execution in medical imaging. One embodiment comprises the steps of creating and storing a workflow template which comprises a standard form for entering data and activities, filling out the workflow template with data and a sequence of activities, and executing the sequence of activities according to the workflow template. A user interface allows the user to input or select preloaded or pre-set settings for carrying out the said method.

All the above control systems apply only for a specific limited part of the activities connected with acquiring, reconstructing, processing and storing and archiving diagnostic images acquired with an MRI imaging system. The interfaces are directed to highly skilled users and the functions and setting parameter are not expressed in terms of the results to be obtained on the image, but in terms of the mathematical geometrical and physical variables connected therewith. This renders the user interface obscure for many non-specifically trained users and obliges to provide for highly specialised users increasing the costs of the diagnostic imaging process.

Furthermore, also specifically trained and highly specialised users have difficulties in using interfaces of MRI scanners from different producers without a training which is focussed on the specific MRI system As it appears also from the cited documents which are only some examples of the existing control systems and user interfaces, the image processing tasks such as CAD systems are provided by third parties or delocalized processing servers which are not part of the control system of the MRI system and which provide an user interface which allows merely to request a service to the delocalized Image processing and CAD server without enabling the user to access or control the image processing and CAD tools.

Prior art standard control systems for MRI systems are based on controls, such as menus or buttons identified by icons or text which are not logically correlated to final image appearance or the identification and eventually the interpretation of features which are present in the acquired images. At the end of the process the radiologists are interested in the results of the image acquisition and of the image processing step which is normally identified by the effect applied to the image or image data and not in the specific techniques used for acquiring, reconstructing and processing the images or the image data. In current control systems the user interface is such that it is the operator/user who has to translate his experience/know-how in proper system's settings adapted to the real-time scan needs. The current image end user controls are based on standard workflow setting parameters which are more related to the physics of the imaging process and to the mathematics of the image processing tools or to physiology and biology than to the final appearance of the images visualized on the display. For doctors or paramedical operators which have a limited knowledge of the system workflow and of the physical processes governing the imaging it is often difficult to influence the image appearance by controlling the values of the said standard workflow setting parameters. Furthermore, many different standard workflow setting parameters have an influence on a certain feature of the image acquisition process and/or of the image processing and/or of the image and patient management so that the operator has to control several different setting parameters directed to several different technical and non-technical fields.

As it appears from the current state of the art, User interfaces with the MRI apparatus have a very technical interface which requests a deeper knowledge of the architecture and way of operating the apparatus in order to be understood and navigated.

This is a drawback because it prevents that service persons at paramedical level can use the MRI scanner by correctly choosing the settings for obtaining diagnostically useful images.

Due to the world-wide trend to reduce health costs by avoiding to employ high degree trained persons for carrying out tasks which could be executed by persons having a lower level of preparation it is an important and strategic choice to develop user interfaces which are more and more user friendly and helps the user either intuitively or by simple tutorials to be able to service the apparatus and correctly acquire diagnostic images.

Furthermore, reduction of times from the start of the examination to the evaluation of the examination and the management of the patient files is important since due to the physics of the imaging process the duration of the image acquisition cannot be reduced in a simple way. Thus, dead times of the non-physical steps and tasks are the key criteria for reducing the global time of each examination and thus rendering the MRI system more effective from the point of view of the number of examination per time unit and of the costs.

SUMMARY OF THE INVENTION

An object of the present invention consists in providing an improved MRI apparatus control system with an improved user interface that is as far as possible intuitive for the user in relation to the functions of the graphic signs such as buttons, menus, actions which can be addressed and activated by the user.

A further aspect of the present invention is to generate a structure of the user interface which is Microsoft Windows® inspired.

A further aspect relates to the fact that a dynamic interaction between the records in a database relating to single cases of the same patient or of different patient, which allows to address the record of a database to which a visualized image or data report belongs by simply clicking on the image or report or by visualizing the said image or report.

This allows a user not to be obliged to follow backwards the path of an image file or data file opened on screen in order to get to the record were all the files related to the opened file are stored but to be directly linked to the said record.

A further aspect consists in providing an MRI system comprising an MRI control system and a control system user interface according to one or more of the above disclosed aspects and objects.

In relation to improving the user interface an embodiment provides for a MRI control system with a user interface which is Microsoft Windows® inspired and comprises active labels that are univocally related to specific examinations or classes of tasks, each active label opening a specific window and the task or examination specific window being provided with context configured toolbars, comprising active buttons, task or examination specific menus.

According to an embodiment, the each task or examination specific window is divided in different areas:

one main area for visualizing reports and/or results of the examination or task, such as acquired images, patient data, results of image processing tasks, scout images, reproduction of constructive parts or setting organs of the scanner on which setting operations has to be carried out, reproduction of the graphical appearance of images sequences, at least one further area of the window for representing the workflow data of the task and the examination being carried out and/or to be carried out and the status of the workflow of the steps related to the task and/or the examination related to the displayed windows;

According to a further embodiment in combination with the above at least one main area and at least one further area the windows may be configured to provide for at least one area for displaying specific menus and/or tools and/or task or examination contextualized help communications or FAQs;

According to still a further embodiment the window may be configured to provide for at least one further area for displaying the dynamic and interactive structure of a database or the tree representing the structure of a file system of a logic memory unit comprising respectively data records or data files and/or image files related to patients, the examination which has been carried out for a specific patient, the examinations scheduled for the specific patient, the reports on the examination carried out for the specific patient, image files or image sequence files generated as an output of the examinations carried out on a specific patient, output files comprising reports and/or images of image processing carried out on the acquired images or sequence of images in an examination carried out on a specific patient the representation of the database structure and/or of the file system structure comprising icons univocally related to a folder and to a file path addressing the location of the folder and the file in the database structure and/or in a file system of a memory in which the folder and files are created and stored According to still a further embodiment the user interface of the MRI control system allows to activate different windows each one for a specific examination and/or task which are displayed overlaid one on the other and being provided with lateral labels for changing the display order and bringing in the foreground the corresponding windows.

Alternatively, some of the windows may be displayed one beside the other at the same time.

According to an embodiment, two or more display areas of a window may be activated at the same time and displayed one beside the other or overlaid one on the other each different representation sharing the same display area being provided with a label allowing to bring the corresponding representation in the foreground.

The interaction with the active buttons, toolbars, ribbon bars, labels and with the icons of the tree structure of the database and other active elements of the user interface can be carried out by point and click operations carried out by means of a pointing device as a mouse, a pen or touchless devices or directly with the hands or a tool by touching the screen of a display.

According to a further embodiment the MRI control system comprises a file path manager and tracker carrying out an automatic dynamic interaction between the records in a database and/or data or image files in a file system of a logic memory unit relating to single cases of the same patient or of different patient and address the record of a database or the file path in the file system to which a visualized image or data report belongs by exercising a selection action on the visualized content of the file such as an image or data of a report or by simply opening the file for visualizing the said image or report.

According to a further embodiment, which may be provided alternatively or in combination with the above disclosed embodiments and which attains to a different aspect, the control system of an MRI system comprises:

a memory for storing a database;
the database comprising records containing data organized according to a database structure;
the memory being configured according to a file system comprising files and folders organized in a tree structure;
the data in the database records and the data files or the image files being univocally addressable by a path and a file name indicating the location of the data or of the files in the database structure and/or in the tree representing the file system structure;

the said file system and/or the structure of the data base being represented by a tree in which each folder is represented by a folder icon and/or name and each file is represented by a file icon and/or name;

the icons being active buttons which provides access to the representation of the content in a folder in form of further folder and/or files and/or opens a file and/or activate management tasks on the folder and/or the files and/or visualizes the content of each opened file on a display;

the control system being provided with a path manager and tracker, generating a link between each visualized file and configured to save the file specific path and to address automatically the file location in the representation of the structure of the database and/or in the file system representation to which the visualized file content belongs by carrying out a selection activity such a point and click operation on the area in which the file content is displayed.

According to a further embodiment the icons provided in the tree representation of the records and of the file system are activated in order to carry out a corresponding function by selecting and starting the function such as for example with a point and click operation by means of an input tool or directly by touch or with other tools such as gesture recognition tools for in putting commands or vocal interfaces.

According to an embodiment, the standard DICOM is applied for the database management and the file format of the data and image files.

According to an embodiment when creating new records comprising new folders, new data and or image or CAD files, the path manager and tracker assigns automatically a path to the said folder and/or file and/or record according to the structure of the database and/or of the file system.

According to a variant embodiment the rules for generating folder and/or files and assigning names to folder and files are set according to the DICOM standard.

According to a further embodiment an MRI system is provided comprising a control unit with a processor executing a control program configuring the said processing unit to carry out the functions of a control system of the MRI system and with a user interface according to one or more of the above disclosed embodiments.

In an embodiment, the MRI system comprises:
a cavity for accommodating a target body under examination or a part thereof
a magnet for generating a static magnetic field in a volume of space;
gradient coils for generating gradient magnetic fields in addition to the static magnetic field according to three spatial directions;
a control unit configured to drive and control the gradient coils and the magnet;
a transmission antenna connected to an excitation signal sequence generator for transmitting spin echo excitations signals into the cavity housing the target body;
a receipt antenna for receiving the MRI signals caused by the excitation signals;
an MRI receipt signals processing unit and image generation unit for processing the signals and extracting image data information and for generating the images;
a display unit for displaying the reconstructed images;
a control system comprising a processor executing a software for configuring the control system to carry out the managing of the image acquisition process, of the image reconstruction process the and/or of the processing of the acquired images and/or the managing of the patient data and the image and data storage process;
the said control system comprising a user interface for input of commands and visualization of data and/or images;
the control system being provided with a data and image files path manager and tracker configured to dynamically link the visualized images or data of a file with the path of said file in a file system and/or database structure where the file is saved;
the said user interface being provided with a display area in which the tree structure of the database and/or of the file system is represented comprising icons representing folder and the files of the database and/or file system structure and in which the icon of the file is automatically highlighted and selected when the said file is open and the content visualized in foreground in a further display area for the said file content.

According to a further embodiment, the user interface control program is executed by the control system and configures the said control system for displaying the user interface on the display screen.

According to a further embodiment a method is provided for managing data and image files with a user interface, the said files being saved in a logical memory location defined by a file system structure and/or in a location in the record structure of the database, each file being univocally identified by a file name, a dedicated icon and a path in the file system identifying one or more nested folders in which the file is saved, the said method comprises:
displaying in a dedicated area the tree representing the structure of the file system and/or of the database and highlighting in the representation a file which is open;
displaying the file content in a display area besides the area for displaying the tree structure and in a dedicated window;
automatically updating the tree representing the structure of the file system or the representation of the structure of the database when the windows showing the content of an open file is shifted in a foreground for visualization by high lighting the file name and icon in the said representation of the structure of the file system and/or of the database corresponding to the file content in the window being visualized in the foreground.

According to a further embodiment of the said method the link to the memory location of each currently visualized file is automatically maintained or activated when the file content of the corresponding file is visualized in the foreground.

In an embodiment with the term visualizing in the foreground, it is meant that each file is opened in a dedicated window and when several files are opened at the same time the windows are displayed in an overlaid order and can be shifted in the foreground to be seen by the user by a command.

In an alternative embodiment, the term shifting in the foreground may also mean that a window is selected for example by pointing or by pointing and clicking or by touch on the corresponding screen area when the windows related each one to a different open file are displayed at least for some of the said windows one beside the other.

In a variant embodiment, the file content of different files is displayed in different zones of a common window, the said zones being positioned one beside the other and the term bring in the foreground should be interpreted also as selecting by pointing, pointing and clicking or touching the screen zone coinciding with the display zone of the desired file content or for some of the said file content display area of the screen in a common window.

BRIEF DESCRIPTION OF THE DRAWINGS

FIG. 6 and FIG. 7 show an example of a of a file system tree in which data or image files are stored which representations are visualized in a dedicated area of the user interface.

FIGS. 17A to 17C, 18A to 18C and 19A to 19D are enlarged views of FIGS. 17 to 19.

DETAILED DESCRIPTION OF THE DRAWINGS

Figure 1:
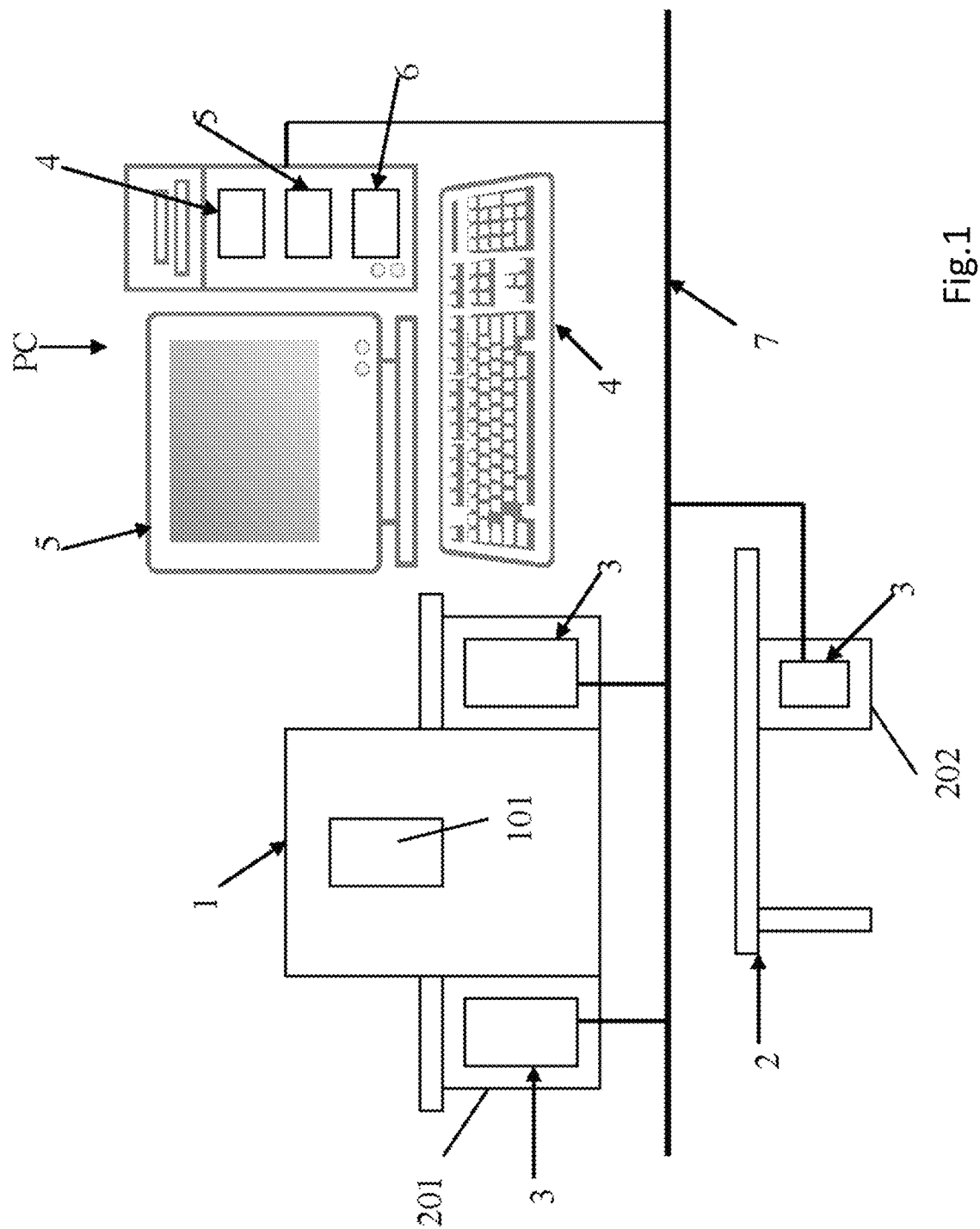
FIG. 1 is a schematic block diagram of an MRI system according to an embodiment.

With reference to FIG. 1, an embodiment of Nuclear Magnetic Resonance imaging apparatus comprises a signal exciting and receiving unit consisting of a magnetic unit 1. The magnetic unit includes permanent or resistive or superconducting magnets for generating a static field inside a cavity 101 which is designed to receive the patient body or a part thereof, particularly a limited anatomic region, such as a leg, an arm, the head, etc.

As is generally known, different coils are associated to the static field generating magnet, including:

excitation coils, for exciting nuclear spins;

magnetic gradient generating coils, for selecting the section plane along which imaging has to be performed, for encoding nuclear spins to univocally identify the signals transmitted at a predetermined space position and univocally assign the received data to a predetermined pixel of a pixel matrix which forms the displayed image;

receiving coils, for receiving magnetic resonance echoes.

Also, other means are provided, such as temperature control sensors and/or means for heat increase or generation and means for heat dissipation, which are designed to set and maintain a predetermined operating temperature, etc.

All the above elements are well-known and widely used in Nuclear Magnetic Resonance imaging machines of any type and size, both for total body machines, i.e. those designed to accommodate the whole patient body or a substantial part thereof, and for dedicated machines, i.e. those adapted to only accommodate specific limbs or limited parts or regions of the patient body.

The geometry of the magnetic structure, i.e. of the cavity for accommodating the body under examination or the part thereof may also be of any type, and particularly either of the open C- or U-shaped type, or consisting of two poles separated by columns, or of the annular, closed type.

The machine shown in FIG. 1 is a non-limiting exemplary embodiment having a closed, i.e. annular magnetic structure and the cavity is only open at the two end sides transverse to the axis. C or U-shaped magnets have three open sides, while other magnets are formed by only two opposite poles which limit a gantry being opened along the peripheral sides of the two poles. Also magnets comprising a limitation only on one side which is formed for example by only one pole plate, the object to be imaged being placed on one side of the said pole plate which is completely exposed to free environment.

In an embodiment a patient table or seat, which may have any construction and is denoted with numeral 2, is generally associated to the magnetic unit. Several embodiments of the patient table or seat are possible. According to one embodiment, the patient table or seat 2 may have a structure adapted to form closable housing compartments, as is schematically shown in FIG. 1. According to other embodiments the patient table may be in the form of a movable table having wheels and/or combined with elevator means and/or combined with means for changing the configuration of the table and/or a table having at least one table plate which is tiltable in order to be oriented along several directions, such as for example in the tables for carrying out weight bearings examinations.

The magnetic unit or structure, with the components listed above, is associated to a control system comprising control, monitoring and processing units, which have the function to control and adjust the various components of the magnetic structure and to receive and process echo signals to extract therefrom all data useful for the reconstruction thereof into an image formed by an array of light image dots, the so-called pixels, whose brightness and/or color are univocally related to the received data and whose position is related to the position, within the body part under examination, wherefrom the echo signal was transmitted.

According to an embodiment the MRI system comprises an electronic unit 3 for controlling the signal exciting and receiving devices, a unit 4 for entering commands to the signal exciting and receiving unit, a display and image processing unit 5 and a filing and storage unit 6 are associated to the magnetic unit.

In the present embodiment of FIG. 1, the unit 3 for controlling the signal exciting and receiving devices is at least partly contained in the case of the magnetic unit 1 and/or possibly also at least partly contained within the structure of the patient table 2, in one part thereof 202, for instance a support column, having the form of a switchboard.

The units for entering commands 4 to the signal exciting and receiving units, for display and image processing 5 and for filing and storage 6 are included, partly as hardware peripherals and partly as software programs, in a traditional personal computer.

The communication between the unit 3, contained in the case of the magnetic unit and/or in the structure of the patient table, with the units 4, 5, 6 of the control console provided by the personal computer is obtained by means of a communication bus denoted with numeral 7.

The communication bus may be of any type, e.g. a conventional communication bus of the Ethernet type, of the SCSI or USB type or of any other type, which allows multiplex communication among several units.

Once the type of bus to be used is selected, the implementation of interfaces with the bus 7 on the individual units 3, 4, 5, 6 is well-known in the art.

The above electronic units may be formed by specific developed boards which circuits are dedicated to carrying out the specific tasks or by generic hardware which comprises processors configured to carry out program instructions which enables the generic hardware to carry out the specific tasks.

Electronic units may be produced according to several techniques available for the construction of electronic boards and circuits.

Different programming languages and operative systems may be employed for generating the control programs providing the processors to execute the instructions for carrying out the specific tasks, such as for example Microsoft Windows NT® based program languages or similar.

Figure 2:
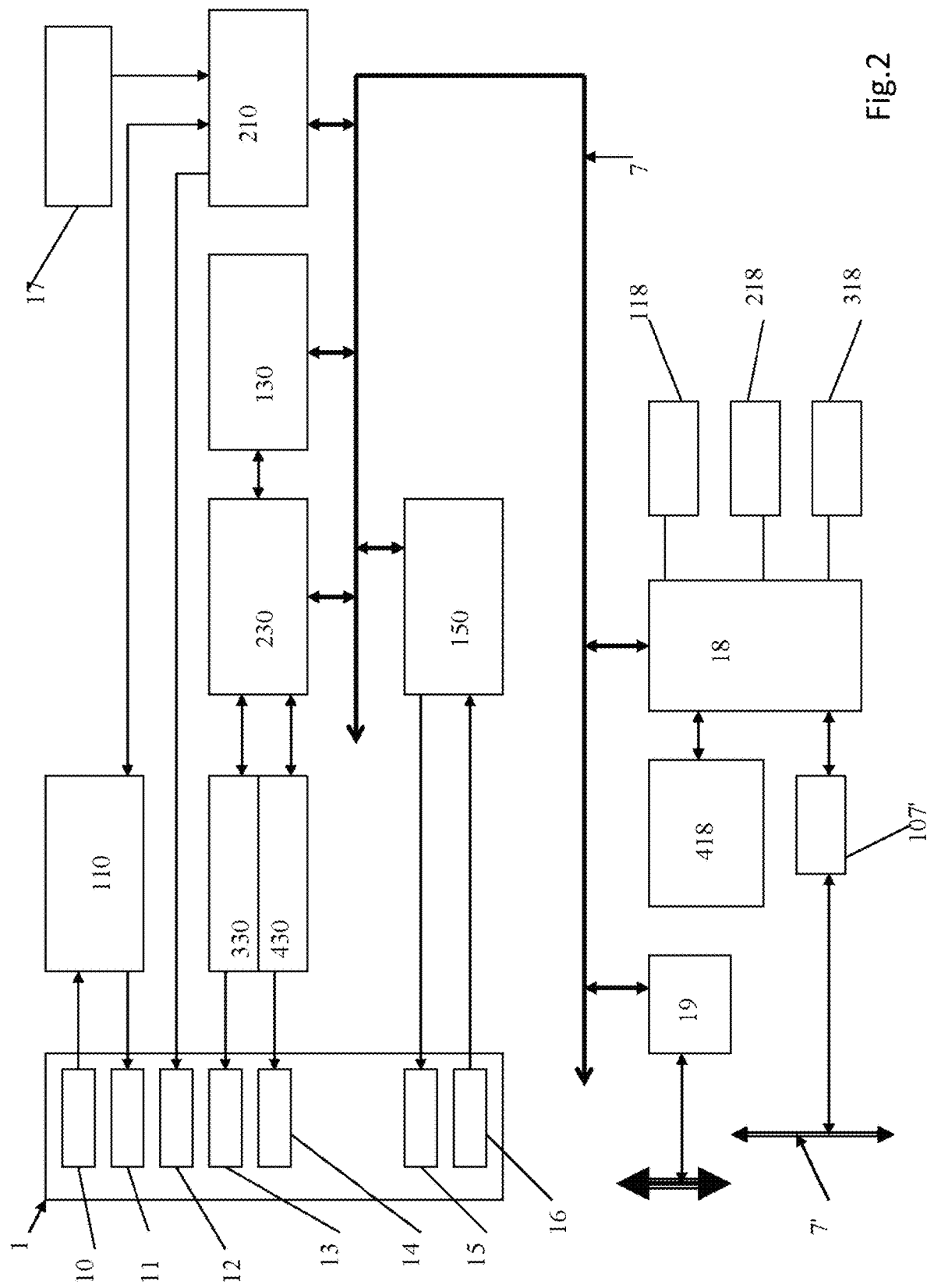
FIG. 2 is a more detailed block diagram of an embodiment of an MRI system.

FIG. 2 shows a block diagram of a higher level embodiment of the generic embodiment of FIG. 1. In this embodiment, the magnetic unit 1 includes several components, as shown in the figure, that is, in addition to static field generating magnets, temperature sensors 10, heating and/or cooling means 11, at least one compensation coil 12, at least one transmission or excitation coil 13, one or more gradient coils 14, tuning means 15 and at least one receiving coil 16, as well as one or more magnetic field sensors 17.

The temperature sensors and the heating and/or cooling means are controlled by a temperature control unit 110 which includes means for reading the signals of the sensors 10 and means for supplying the heaters and/or coolers 11, which are controlled by a thermal control unit 210 based on the actual detected temperature and on the comparison thereof with the preset nominal values.

The thermal and magnetic control unit also controls the compensation coil 13 to correct the static magnetic field with reference to the variations induced therein by external magnetic fields and based on the actual field values detected by the magnetic field sensors 17. A supervision, pre-processing and reconstruction unit 130 controls a data capture and control unit 230 which in turn controls the amplifiers 330 and 430 for the signals provided to the transmission or excitation coil 13 and to the gradient coil/s 14 respectively. A receiver unit 150 is responsible for tuning 15 the receiving coil 16 and identifying the receiving coil 16, as well as for receiving the data collected by said receiving coil 16.

According to an embodiment these units are all contained wholly or at least partly inside the case of the magnetic unit, and/or wholly or at least partly in a closable compartment of the structure of the patient table. According to a further embodiment these units may be all or at least partly formed by a traditional PC running a program in which instructions are coded for controlling the PC processor or processors in order to carry out the functions of the said part of units.

According to an embodiment, the supervision, pre-processing and reconstruction unit 130, the control and data capture unit 230, the thermal and magnetic control unit 110 and the receiver unit 150 communicate with one another and/or with other units by means of a bus 7.

More particularly, these units communicate with the CPU 18 of a conventional personal computer, having conventional peripherals, according to the desired or required quantity and type. The display and command entry peripherals denoted with numerals 118, 218, 318, as well as a mass memory for filing and a memory for the specific image processing and display software, collectively denoted with numeral 418 are connected to the CPU 18.

According to another embodiment, the CPU 18 may also communicate 107' in turn with a local communication network 7', such as a LAN network within the hospital or an Intranet or Internet network, or a network of any other suitable type. The communication bus 7 is also connected with a modem unit 19, which allows connection to a local network and/or to other machines connected to the local network via a telephone line. This redundancy, besides allowing to communicate with local networks in other locations, is also an alternative method for connection with the local LAN network, in case of temporary communications problems of the network interfaces.

As is apparent from the above description, the communication bus is not only provided between the individual units, but is also extended inside the latter, thereby providing the greatest configuration and operation freedom as well as allowing to add functional units with new functions and/or to replace old type units with more modern units. Replacement operations, both for upgrading and repairing purposes are apparently easy. As long as signals are encoded consistently with the bus in use, any unit may be connected to the communication bus 7 and is able to exchange data and commands with the other units.

The above disclosed exemplary construction of the apparatus allows additional configurations, which might be highly advantageous in terms both of cost effectiveness and of organization and management. In fact, the connection of various units through a conventional data bus allows to control several apparatuses, even of different types, but all having the same configuration as the processing and control electronics, from a single location or from a limited number of locations.

According to a further embodiment, a system may be also provided which comprises several machines organized in groups, each having a single dedicated console in the form of a conventional computer, each conventional computer associated to each group being configured as a client computer, which accesses a server computer via a network. In this case, the server computer may contain many different programs for controlling image acquisition and/or processing and reconstruction procedures, e.g. a database of Nuclear Magnetic Resonance imaging sequences, a database of signal filtering and/or processing procedures aimed at modulating the definition and/or the contrast and/or the signal-to-noise ratio and/or the imaging times, whereas the client computers may access the server databases to extract programs and/or image acquisition and/or processing procedures from said databases.

By this arrangement, client computers may be configured in a more inexpensive manner, especially as regards memories and graphic sections. Also, limited-quality means, e.g. monitors or printers, may be provided locally, while higher-quality means are associated to the server. This provides considerable resource savings, and allows, for instance to purchase higher-quality monitors and/or other display means, such as printers or the like.

Figure 3:
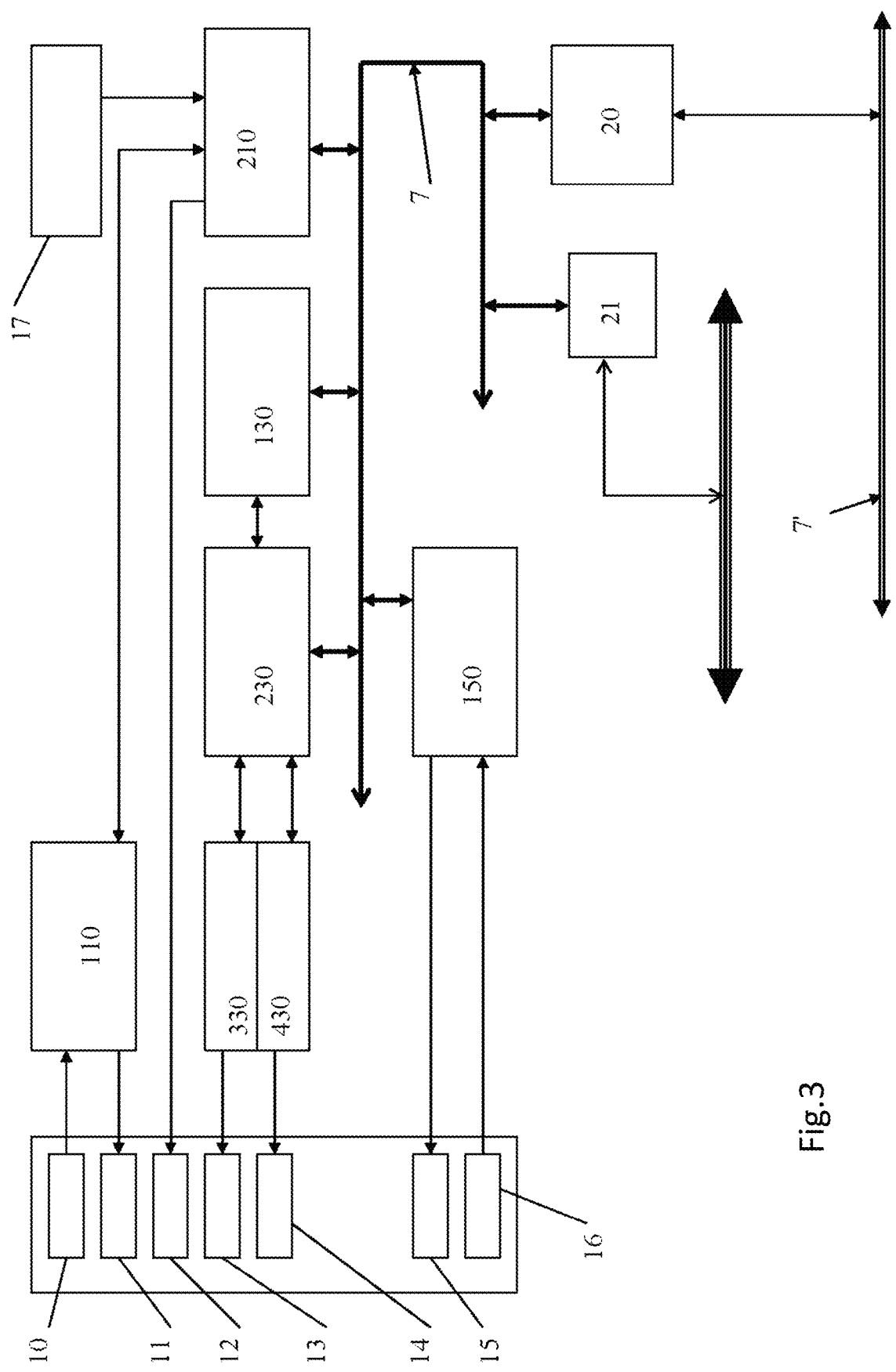
FIG. 3 illustrates a block diagram to a further embodiment of an MRI system.

A further configuration example of an MRI system according to the invention, fit for this configuration, is shown in FIG. 3. Same functions or means in this figure are denoted with same numerals. As is evident from the comparison with FIG. 2, the units that are expressly dedicated to the control of the magnetic unit and to the reception of echo signals, as well as to signal processing to extract image data are identical to those described with reference to FIG. 2. However, unlike the previous example of FIG. 2, the apparatus has no dedicated console, but includes a local CPU unit which controls the communications between the internal bus 7 and the communication bus, e.g. a LAN network or the like, denoted with numeral 20. A modem 21 may be provided to allow communication via telephone lines. The local CPU 20, whereto local memories may be associated, accesses a local computer via the LAN network, which local computer integrates the units as described in FIG. 2 and is designed to control several machines. As mentioned above, the local computer may in turn be a client computer of a server computer for generally controlling several groups of apparatuses. The presence of an internal controlling CPU 20 does not cause a real cost increase, both due to the comparatively little cost of CPUs and to the fact that this configuration allows to reduce the number of computers dedicated to the control of machines.

Moreover, according to a further embodiment, the local CPU may be used to also control local peripherals, such as storage, display, print and control entry means.

It shall be noted that the presence of a local CPU 20 does not even hinder the possibly desired provision of one or more machines having a dedicated console.

Figure 4:
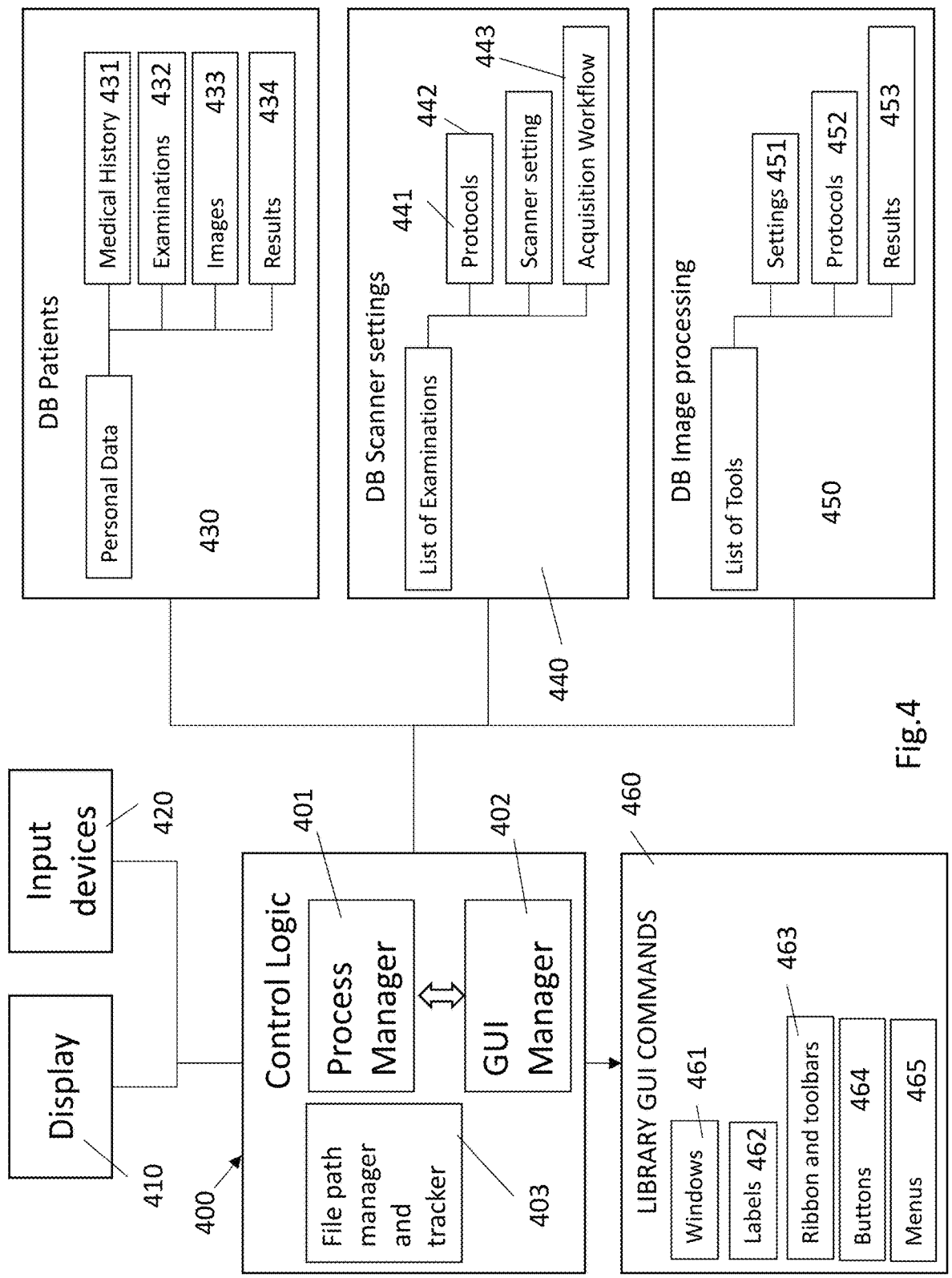
FIG. 4 is a block diagram of a control system for an MRI apparatus.

FIG. 4 is a block diagram of a control system for an MRI apparatus. A control logic 400 comprising a process manager 401 which manages the different processes which may be carried out by the MRI system.

According to an embodiment the said processes are the MM apparatus settings for carrying out image acquisitions, the processes for carrying out image acquisitions, the settings and the processes of generating and managing a database for recording the personal data of the patient, the data relating to the examinations carried out or to be carried out and the image files acquired.

Furthermore, the control logic 402 manages the user interfaces and particularly the graphic user interface which is displayed on a screen 410 and the input devices 420.

According to an embodiment, the control logic is in the form of a processor executing a control logic program which configures the processor and the peripherals controlled by the processor to carry out the steps for managing the workflow of the processes needed to carry out the imaging tasks and the other tasks related to the further functions of the MRI apparatus including processing of the acquired images according to CAD tools.

An embodiment of the processes is represented in FIG. 4 by the generated corresponding database which can be addressed for retrieving data or updated for modifying existing data or adding new data.

A patient database 430 comprises personal data of the patients the personal data may for example comprise the medical history 431 of the patient, the examinations 432 carried out and the corresponding acquired images 433 and the results 434 of the examinations.

According to an embodiment a Scanner Settings database 440 comprises lists of standard examinations which may be carried out by the MM system and comprising pre-set imaging protocols 441, scanner settings 442 and image acquisition workflows 443. The database is accessed by the process manager for being set to the disposition of the user in the user interface. Furthermore, the data may be also modified or new data may be generated and recorded in the database as new settings new examination or new protocols.

According to an embodiment the control system of the MRI apparatus may provide also for accessing and managing the execution and the storage of the results and the corresponding user interfaces of image processing and CAD tools.

According to an embodiment a Image processing database 460 is provided which may be accessed by the process manager 401 in order to render accessible to the user to a corresponding graphic user interface one or more image processing or CAD tools.

In an embodiment, the database of the image processing and CAD tools 450 may comprise a list of tools in which data 451 about the settings of the tools, protocols 452 for applying the tools to image data and report format and storage processes 453 of the results of the image processing.

In relation to the embodiment of FIG. 4 the lists described for the content of the databases and of the library as well as for the structure of the control logic are not exhaustive and many modifications are possible depending on the configuration choices made by the skilled person.

Through the graphic user interface 402, the process manager 400 generates input and output windows on the display 410 by combining graphic elements which corresponds to active input or selection areas on the screen in order to generate a screen windows structure which corresponds to a certain process step or tasks and to the corresponding data provided from the databases 430, 440 and 450.

According to an embodiment pre-set elements of the graphic interface forming in combination an interface window on the display 410 are stored in a library 460 and may be recalled by the GUI manager 402 to generate and manage a representation of the interface which is constructed according to the current task or process carried out by the process manager 401.

According to an embodiment the process manager 401 can allow to create new patients, new examinations, new protocols new settings, new workflows and new image processing methods and tools and the GUI manager 402 will allow to generate new interface elements or modify existing interface elements related to the said new patients, new examinations, new protocols new settings, new workflows and new image processing methods and tools which are added to the library 460.

According to an embodiment according to a non-exhaustive list, the elements of the graphic user interface stored in the library 460 may be windows frames 461, labels 462, ribbon and tool bars structures 463, buttons 464 and menus 465.

As it will appear more clearly from the following the control logic 400 comprises a further operative unit consisting in a file path manager and tracker indicated with 403 and which records, traces and keeps active the link between the file location in the file system of each file being opened and visualized and which automatically updates the active connection to the physical memory location of the file which content is visualized on the display and/or is at least selected by the user using one of the input devices 420 available for the MRI system.

Alternatively or in combination, the data or images may be stored in a database record and the path manager and tracker will manage and keep trace of the path of the visualized data in a selected window or display area in the location defined according to the structure of the database.

Figure 5:
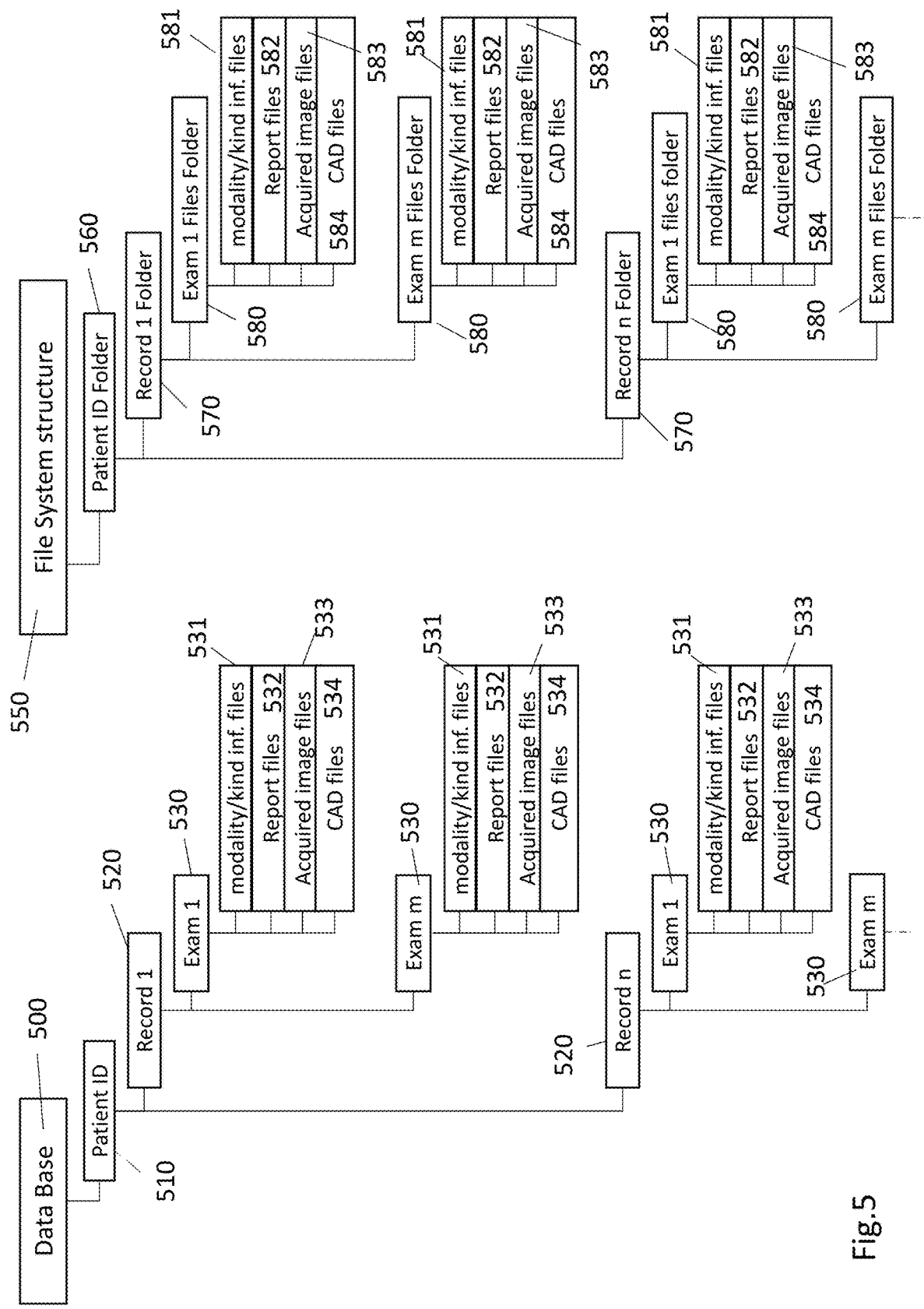
FIG. 5 illustrates schematically a simplified embodiment of the representation in a generic tree form of the database structure and a representation in the form of a tree of the corresponding file system structure determining the memory locations in which the data and images are saved.

FIG. 5 shows a diagram representation of an embodiment of the database structure and of the files system structure determining the location on the memory device where the data and image files are stored and thus the path to this location corresponding to the structure of the tree of the file system and/or the database structure, indicating the logical units and the folders in which the file is allocated.

Database record 500 are structured in providing for each patient 510 one or more records 520 indicated by the index 1 to n where n stands for a natural number. According to a non-exhaustive list each record may contain data relating to one or more examinations 530 identified by the index 1 to m, where m stands for a natural number. According to the embodiment of FIG. 5 each examination record 530 may contain one or more files. The non-exhaustive list of the files illustrated in FIG. 5 comprises files 531 containing information data about the modality or kind of examination, files 532 containing reports relating to the examination activity, files 533 corresponding to the acquire images and files 534 containing the data on the results of image processing tools and/or CAD tools applied to the image and/or result data related to the said examination.

On the right side of FIG. 5 a possible structure of the file system organizing the logical volume and the directories and subdirectories for storing the information files, the result files, the processing files and the image files is shown.

In the logic volume 550 for storing the data and image files, each patient is related to a patient folder 560, for example by naming the corresponding folder with a patient ID code univocally correlated to a physical patient. Inside the patient folder a record folders 570 are created. Each folder is identified by a univocally correlated name and in the FIG. 5 the record folders are identified by the index 1 to n, where n is a natural number corresponding to the number of record folders 570 which in turn may correspond to the number of records 1 to n of the database.

In each record folder one or more exam folders 580 are provided which are identified by a different name univocally related to one folder and which in FIG. 5 are identified by the index 1 to m, where m is a natural number corresponding to the number of examinations 530 in the database structure. A non-exhaustive list of different files may be stored in each examination folder 530 which for example may comprise files 581 containing information data about the modality or kind of examination, files 582 containing reports relating to the examination activity, files 583 corresponding to the acquire images and files 584 containing the data on the results of image processing tools and/or CAD tools applied to the image and/or result data related to the said examination. The logic volume 550 and the sequence of nested folders 560, 570 and 580 are the path of the files contained in the folder 580 to their physical location within the memory, identified by the file system structure of the logic volume and corresponding to the structure defined by the database. So for each file 581, 582, 583, 584 it is possible to generate in a predefined manner the path to the location in the physical and in the corresponding logical storage unit and/or in the database when generating new patients and/or new records and/or new examinations and/or new data or image files 581, 582, 583, 584. Furthermore, for each file 581, 582, 583, 584 it is possible to manage and trace the corresponding path in the database structure and in the file system in a dynamic way so that the path is activated each time an action is carried out on the file content or the file content is printed on scree in a dedicated display area.

FIGS. 6 and 7 shows two examples of the tree structure which is displayed by the GUI manager 402 of the control system in a specific area of the screen of the display. According to the process described with reference to FIG. 4 thanks to the library of icons and other graphic elements for constructing the GUI an intuitive understandable and context or meaning related icon is used for showing a certain folder of the file system and/or for the structure of the database records.

The higher level shown is represented by the patient folder which is indicated by the icon 601. Patient name and other data are associated to the icon representing the patient folder. An active button 602 allows to show or hide the tree of the file system structure inside the patient folder 601. As it appears for each folder icon containing a further folder or files is provided an active button 603.

The record is represented by a folder icon 604. In this case the record icon 604 is identified by the anatomical region to be examined and as far as possible the icon 604 is a stylized representation of the said anatomical region. The folder 604 contains examination folders identified by the icons 605 606 607 which are related to different kind of examination and/or analysis reports.

The content of this folders is not shown and may be visualized on screen by clicking on the corresponding buttons 603. This is indicated by the symbol "+" provided on each button. The symbol "−" indicates that the folder is open and the content visualized and that by clicking on the button 603 the folder content may be hidden again.

The folder 602' shows another record related to CAD follow ups and which is identified by an icon. The content of this record is hidden ads it appears from the symbol "+" on the button 603.

In FIG. 7 a detail of the tree of FIG. 6 is illustrated in which the folder 604 related to an examination generating image series is opened and the files 710 of each image series is shown by a file icon and a file comment or name.

According to an embodiment, the file names or comments associated with the file icon may be generated by using as file name or information to be inserted in the comments certain data od information generated according to the standard DICOM protocol As it is shown in FIG. 7, the image name is associated to the image kind, the data about the FOV (field of view) the image dimensions the repetition times TR, the kind of series and the date and time at which the file has been generated.

According to an embodiment as shown in the FIG. 7, the image files icons are generated by a representation of an image relating to the anatomic district which has been examined and which is a reduced reproduction of one of the images of the image series of the corresponding file.

Figure 8:
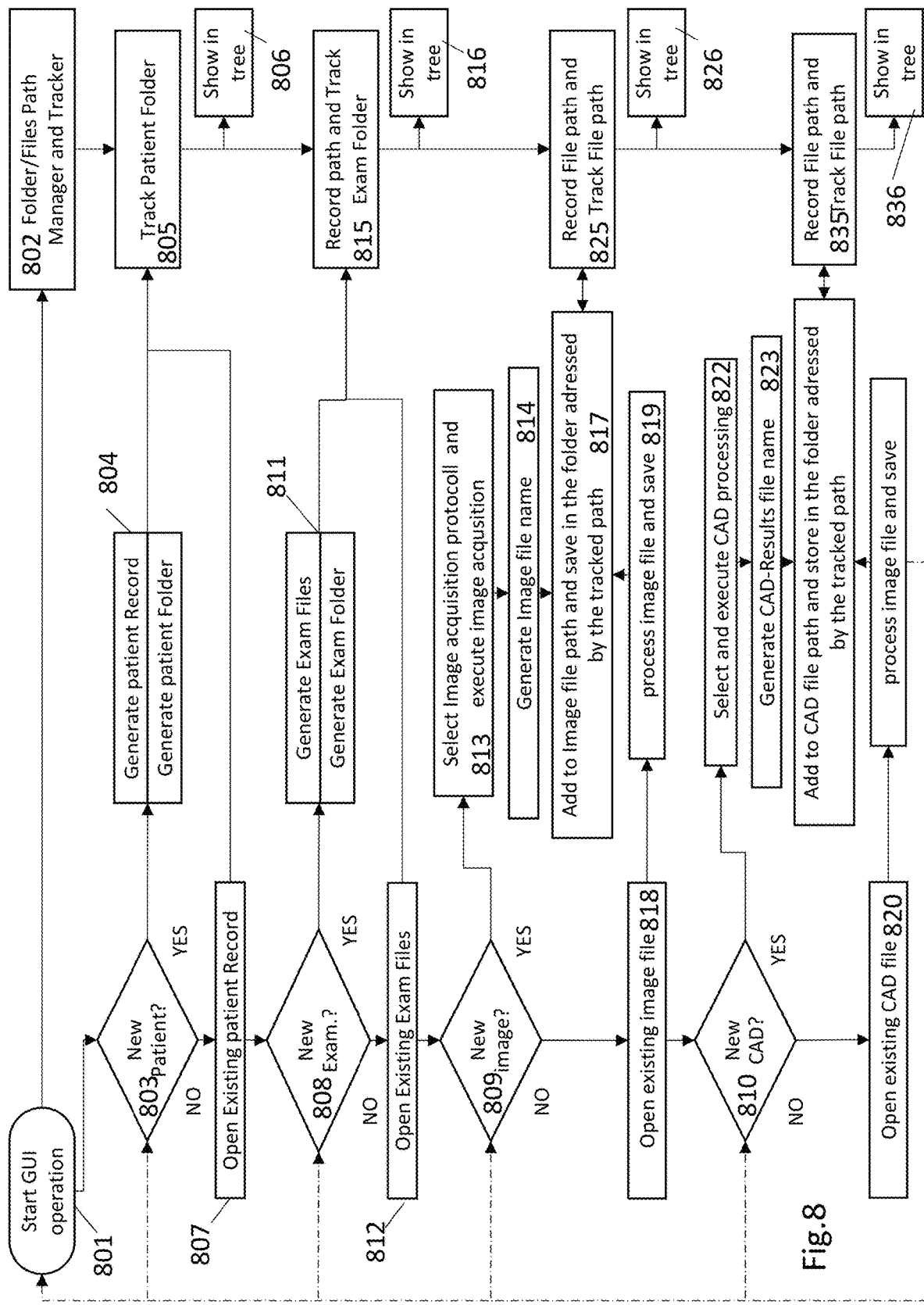
FIG. 8 illustrates a flux diagram of a simplified embodiment of the steps for selecting patient data records for existing patients or generating new patient data for an existing patient or generating a new patient for new patient data and of the steps of managing and tracking the data and image files memory locations defined by a file system structure.
Figure 9:
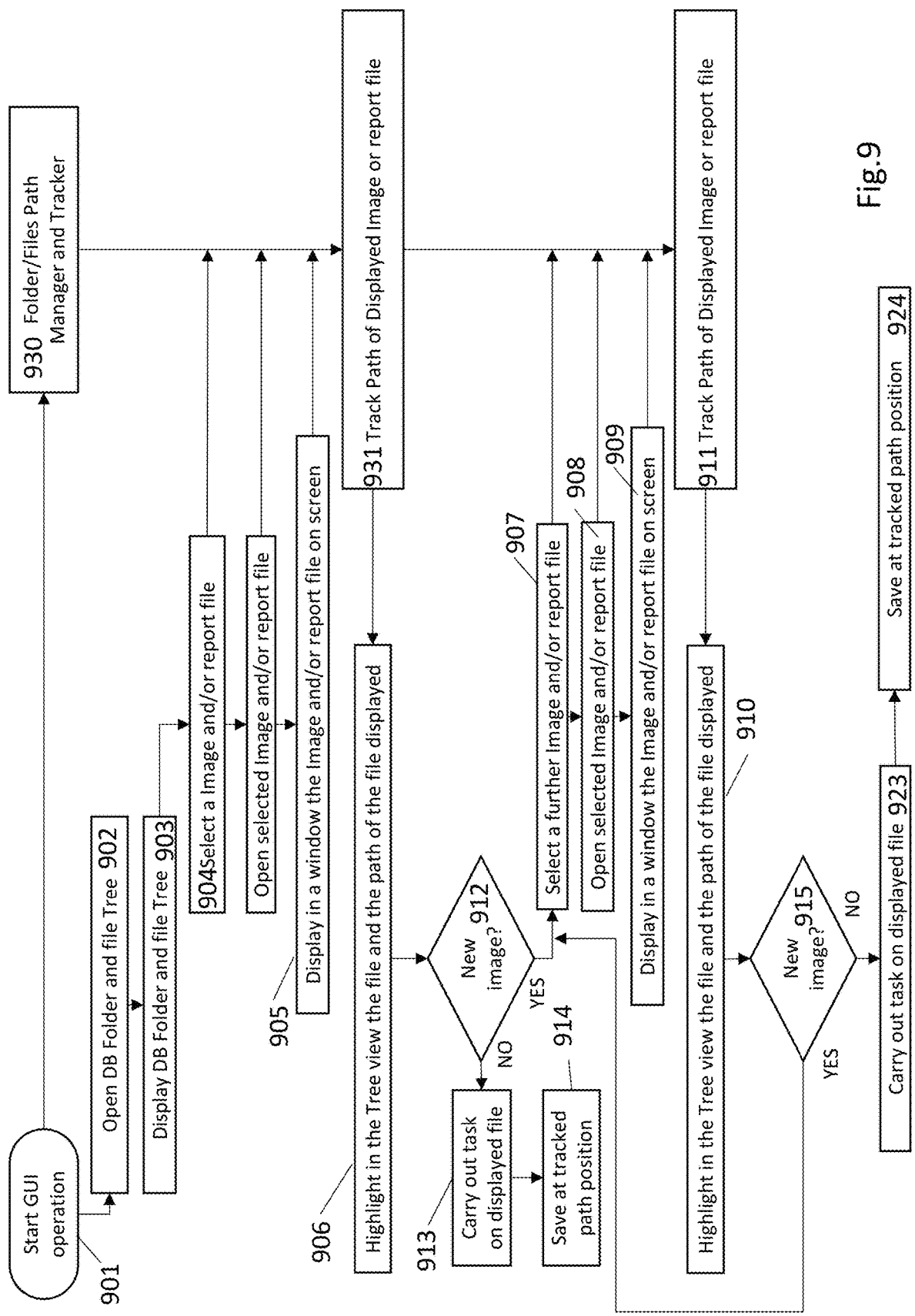
FIG. 9 shows a flux diagram of the steps of visualizing a file content on a display and tracking the file path of the visualized file and saving any change to the visualized file at the corresponding location in the file system defined by the file path.

FIG. 8 shows a flux diagram of an embodiment of workflow of the path manager and tracker provided in the control system according to the embodiment of FIG. 4. At step 801 the operation of the system is started by starting the GUI interface. In parallel the file path manager and tracker is also started at step 802. A decision is to be made at step 803 if the operation regards an existing patient in the patient database or if the operation regards a new patient. If a new patient is to be examined the steps of generating the patient record in the database and the patient folder in the file system is carried out at step 804. The path manager and tracker records the patient folder name and path in the tree structure of the file system and/or of the database and shows it in a tree representation of the file system and/or of the database structure as indicated by the steps 805 and 806. If the patient is already present in the database at step 807 the patient folder is opened, the path manager and tracker tracks the path of the patient folder and visualizes it in the tree structure of the file system and/or of the database as indicated by the steps 805 and 806.

In the following steps of the workflow of the control system according to the embodiment of FIG. 8, a decision has to be taken relating to the fact if the examination is a new one or an already existing one, if the image within a new or an existing examination is a new one or an existing one and if a new image processing step has to be carried out on existing images or on new images or in part on existing and new images or if the file of the data relating to an existing and at least partly executed CAD or imaging process has to be opened as indicated by the decision steps 808, 809, 810. In relation to the examination either a new exam file and a new examination folder is generated at step 811 or an existing examination file is opened as indicated at step 812. In both cases the path manager and tracker records the path of the folder in the file system or the record in the database and shows it in the tree structure of the file system and/or of the database as indicated at step 815 and 816.

When a new image or a new series of images has to be acquired after the decision step 809, according to the present embodiment the user will be requested or suggested at step 813 to choose an image acquisition protocol and to start the image acquisition process which is also managed by the control logic and the user interface. The image or the series of images acquired is univocally attributed an image file name which can be automatically determined by the control system using some of the data or the file header or of the examination description according to the standard DICOM protocol as indicated at step 814. To terminate the image file saving process in step 817 the file representation is added to the tree representation by using an icon and/or the file name generated at the previous step 814. The folder in which the file is stored is the one indicated by the path manager and tracker as the result of the tracking process and the file tracker manager and tracker records the new file name and path related to allocation of the said file in the file system and or in the database and shows the new file in the tree representation of the file system and/or of the database as indicated at steps 825 and 826.

If the operation at the step 809 relates to an existing image file the file is opened at 818 operations on the existing file are carried out as indicated at 819. As the file is opened the tree image is updated by the path manager and tracker by showing in an highlighted way the opened file, The file name and the path of the opened file is registered by the path manager and tracker as shown by the steps 817, 825 and 826.

Similar branching of the operational steps is provided after the decision at step 810 regarding the execution of a new cad process or the opening of an existing process or CAD output file as indicated by the steps 820 and 822. If a new process is to be carried out the CAD or processing tool is selected and executed at step 822. CAD results data files and image files are generated at step 823 and a file name is assigned to the said files. Similarly to the previous steps, to terminate the file saving process in step 824 the file representation is added to the tree representation by using an icon and/or the file name generated at the previous step 823. The folder in which the file is stored is the one indicated by the path manager and tracker as the result of the tracking process and the file tracker manager and tracker records the new file name and path related to allocation of the said file in the file system and or in the database and shows the new file in the tree representation of the file system and/or of the database as indicated at steps 835 and 836.

As indicated by the dotted lines after having ended a first cycle, the steps of the above disclosed process may be repeated at any of the stages provided by the decision step 803, 808, 809, 810 for carrying out a new operation on existing data or generating new data. As it appears clearly by the dotted lines the process may be repeated for a new patient or only for a new examination in relation to a patient already recorded in the database or for a new image or a new CAD processing of an existing image.

The embodiment of figure shows of an exemplary embodiment of the workflow of the control system in managing and tracking the path of different files opened and displayed in a window. Starting the GUI operations, the control logic will open in an area of a display the image of the file system structure and/or of the database structure as indicated by the steps 902, 903. At step 904, through the GUI interface in combination with one or more input devices and image or report file is selected by the user in the file system representation. This may be carried out by pointing and clicking with a mouse pointer on an icon 710 of a file in a file system representation according to FIGS. 6 and 7 after having opened one after the other the folders 601, 602, 603 and one of the folders 605, 606 and 607 in which the file is allocated. Opening the file 710 will cause the system to display the file content such as data or an image or an image loop in an area of the screen or in a dedicated window as indicated by step 905. In parallel to each of the above steps the path manager and tracker which has been activated 930 as a result of the staring the GUI operation at step 901 receives the information on the path of the selected windows and register this path. At step 906 the icon and/or name of the file displayed is highlighted in the representation of the tree of the file system. The process is repeated as indicated by the steps 901 to 911 according to the result of the decisional step 912. If no further file has to be opened, the file is processed or viewed and after being processed or viewed it is closed by saving it at the location defined by the tracked path as indicated by the steps 913 and 914. The repetition of the cycle of steps 907 to 911 can be carried out several times leading to several files which are open at the same time. This is shown by the steps 915. If it is decided not to open further files than the process is ended and the tasks on each of the opened files is carried out by saving the files at the tracked location as indicated by the steps 923 and 924.

Figure 10:
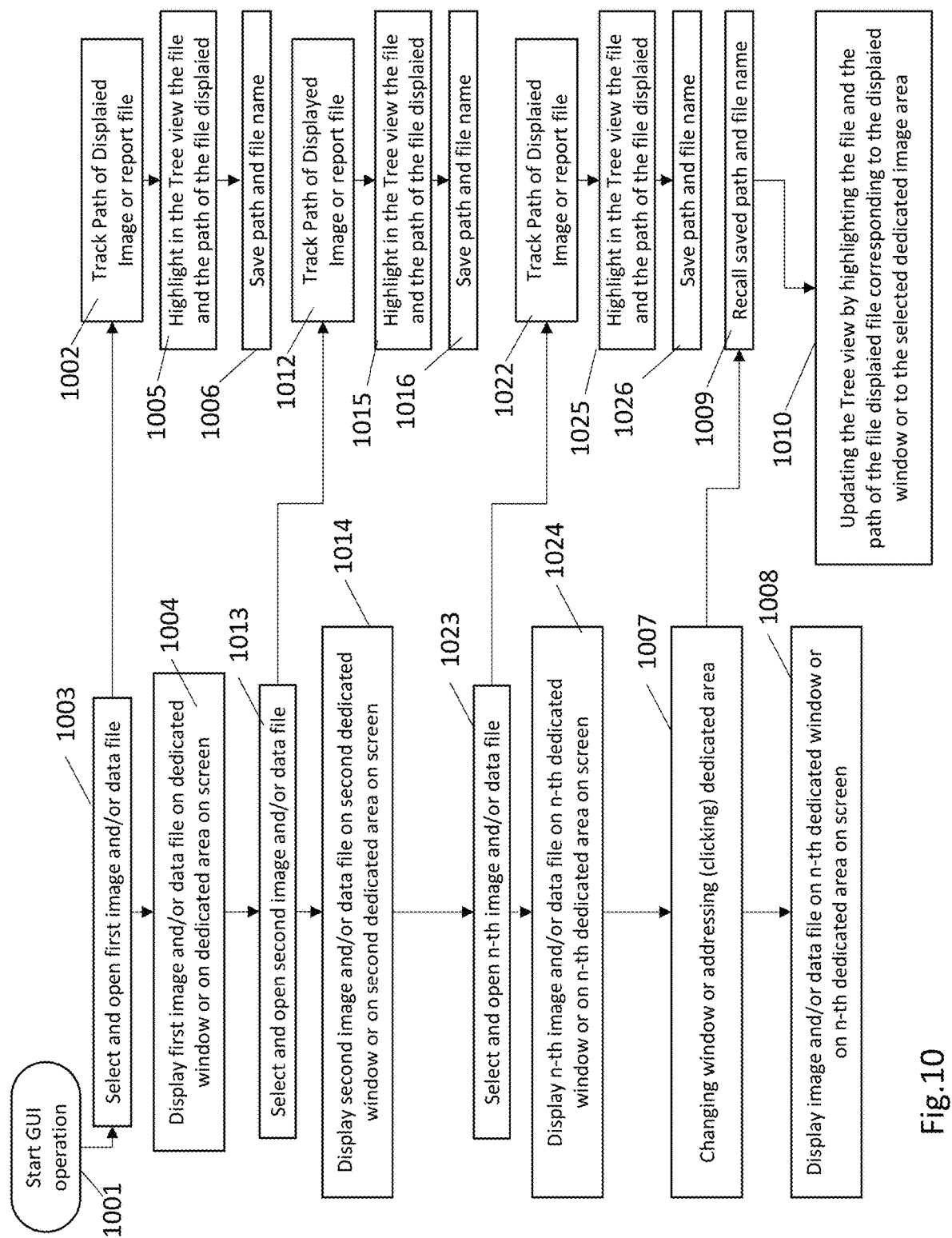
FIG. 10 shows a flux diagram of the steps of dynamically tracking the file path of the memory location for a file in the file system when the corresponding visualized file content is brought in the foreground on the display screen on which the content of several data or image files is displayed each one in a separate windows or display area.

FIG. 10 shows a flow diagram of an exemplary embodiment of the operation of the file path manager and tracker provided in the control system. The GUI operation is started 1001 by a corresponding command. A first image file is selected and opened at step 1003 in the tree representation of the file system for example according to the steps described with reference to FIGS. 4 to 9. The tracking activity of the path manager and tracker is started also as indicated at step 1002. The image or data file content is visualized at 1004 on a dedicated window of the GUI or on a selected delimited area of the screen and in parallel in another area of the screen placed beside the area for displaying the file content the tree representation of the file system is shown and the icon and/or the name of the selected and opened file is highlighted in the tree representation of the file system automatically showing the image of the tree structure of the path represented by the sequence of folders in the last of which the file is allocated. This step is indicated by numerals 1005. At the same time at step 1006 the path manager and tracker registers the path and the file name of the file the content of which is displayed.

The steps 1002 to 1006 are repeated for a desired number of different files as indicated by the steps 1012 to 1016 for a second file and 1022 to 1026 for an n-th file, where n is a natural number. The limit of opened and displayed files depends mainly on the hardware configuration of the control system and on the fact that the performances of the operative system as for example the capacity of the installed RAM memory which can be governed by the operating system and by the hardware.

The content of the different files may be displayed each on a different window which windows are overlaid one on the other and can be brought in the foreground so to be seen by the user by selection and shifting commands provided by the GUI.

Alternatively, or in combination the content of at least some of the files can be displayed in a common window each one in a different area of the window of more than one display zones placed one beside the other. As indicated by step 1007 and 1008, the user or operator is able to shift in the foreground the windows in which the content of a file is displayed or to select a displayed file content on one of the zones in which a common window is subdivided. These steps are sensed by the path manager and tracker as indicated by the step 1009 and the path manager and tracker automatically updates the tree representation displayed in a dedicated area beside the area in which the corresponding file content is shown as indicated at step 1010. At the same time the file path is active so that a saving process of the file is automatically carried out by using the tracked file path and name.

As it will appear more clearly from some examples of screenshots of a graphic User Interface (GUI), the user will not have to navigate the tree representation of the file system each time he visualizes on screen the content of a file or each time he selects the content of a file but the control system will update the tree representation highlighting the file and the path automatically. This allows to simplify many operations particularly when the user is carrying out tasks requiring the comparison of several images for follow up studies or for selection of images or also for comparing images one with the other.

Figure 11:
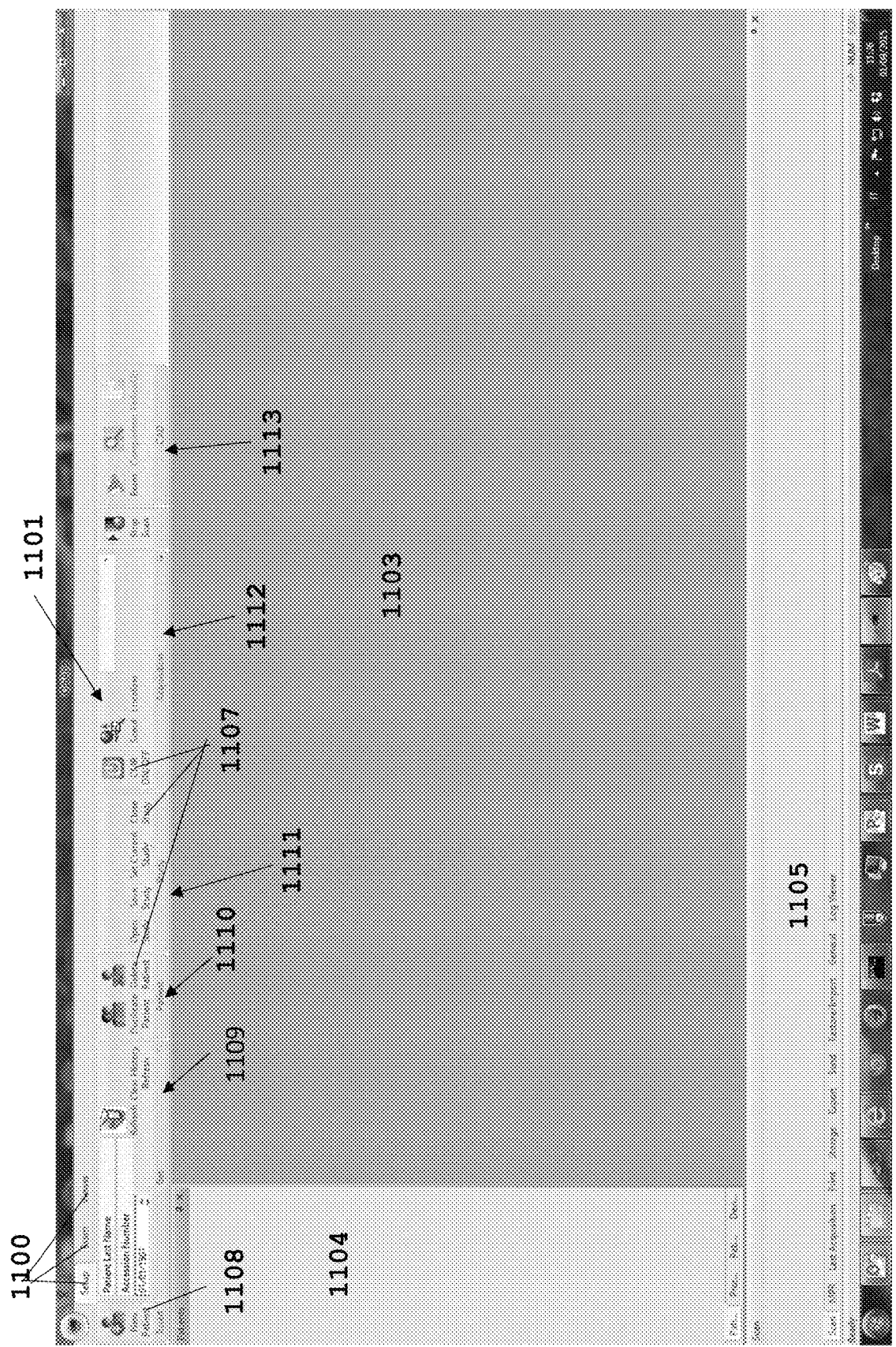
FIGS. 11 to 13 show three screenshots of the graphic user interface displayed on a screen according to an embodiment of the control system for an MRI apparatus.
Figure 11A:
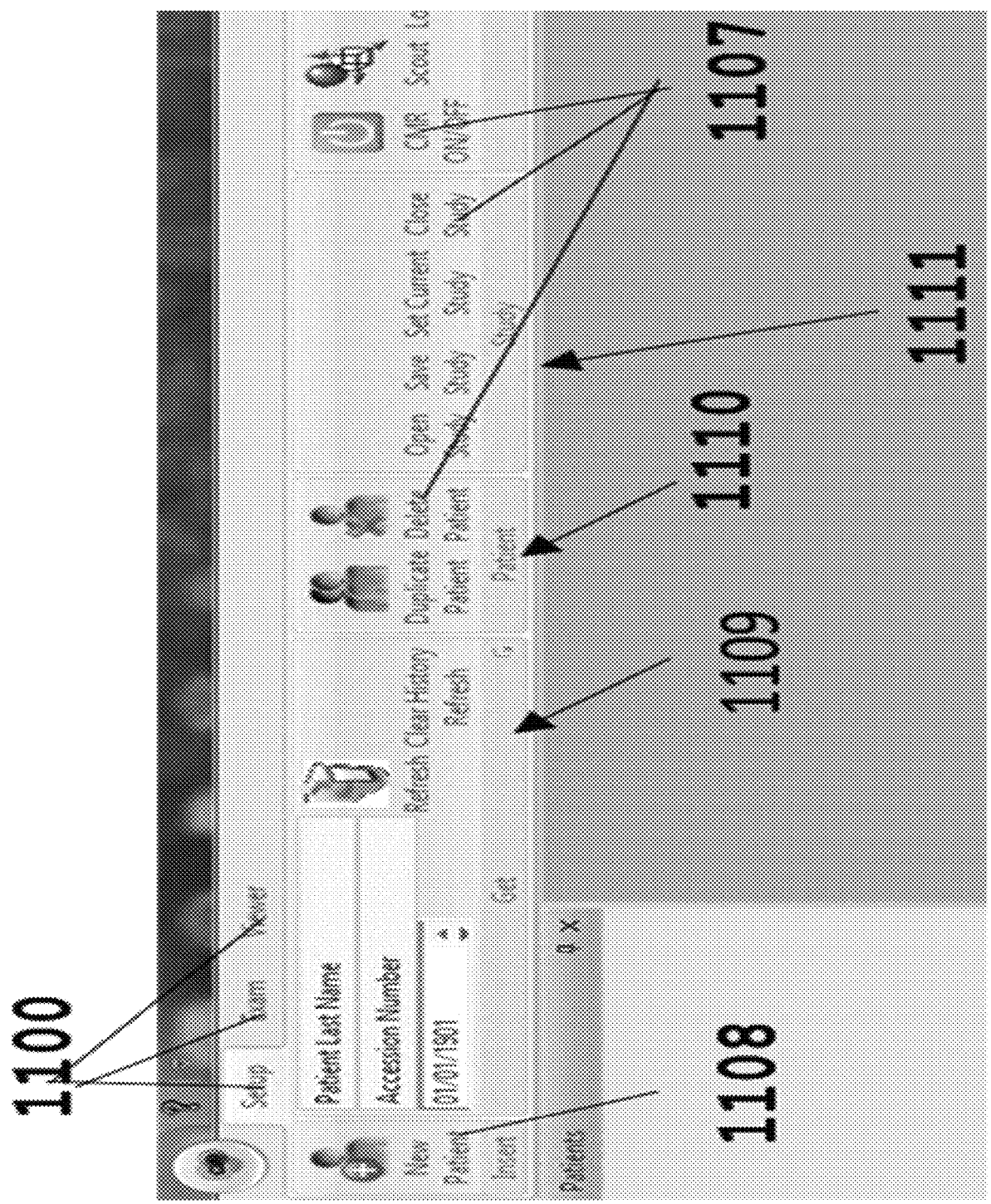
FIGS. 11A to 11C, 12A, 12B, 13A to 13C are enlarged views of FIGS. 11 to 13.
Figure 11B:
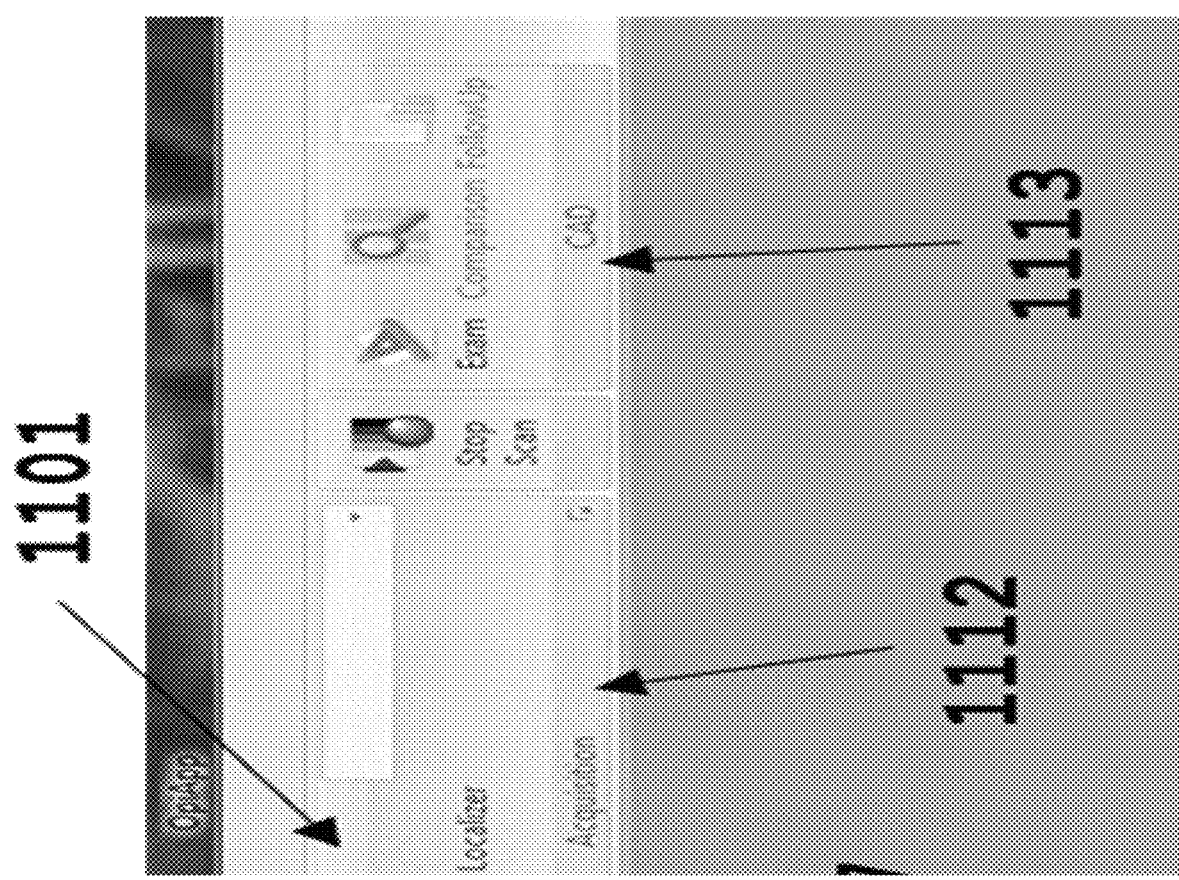
Figure 11C:
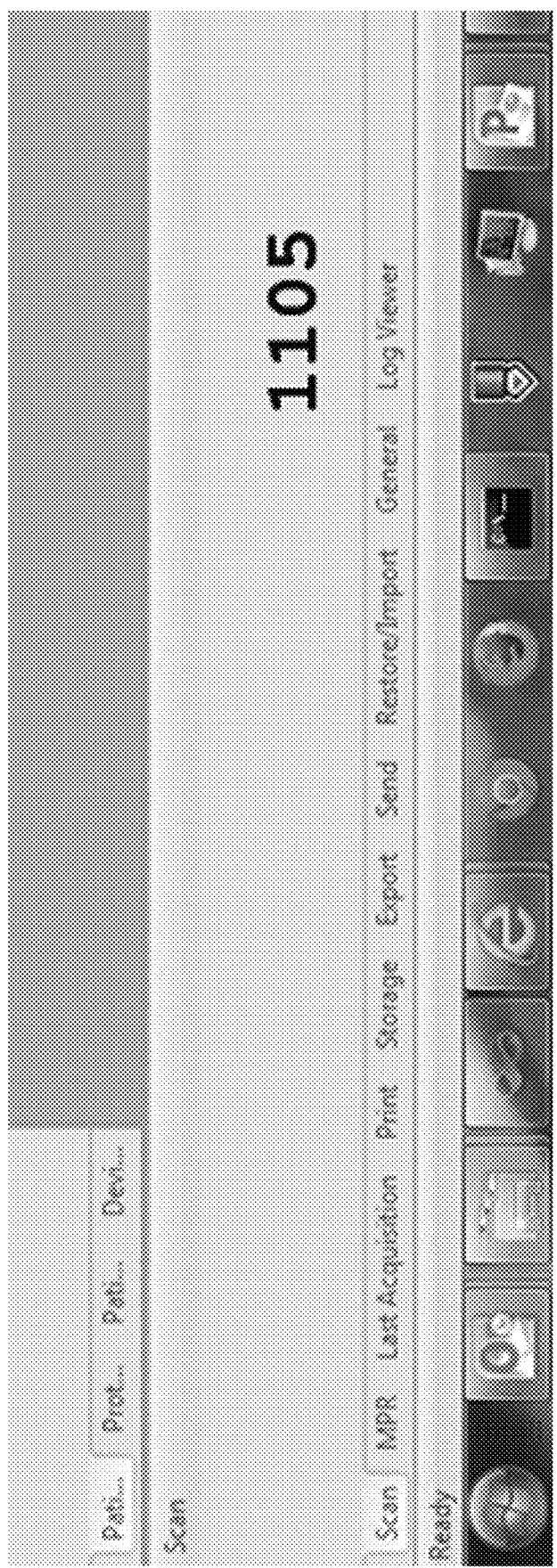
Figure 12:
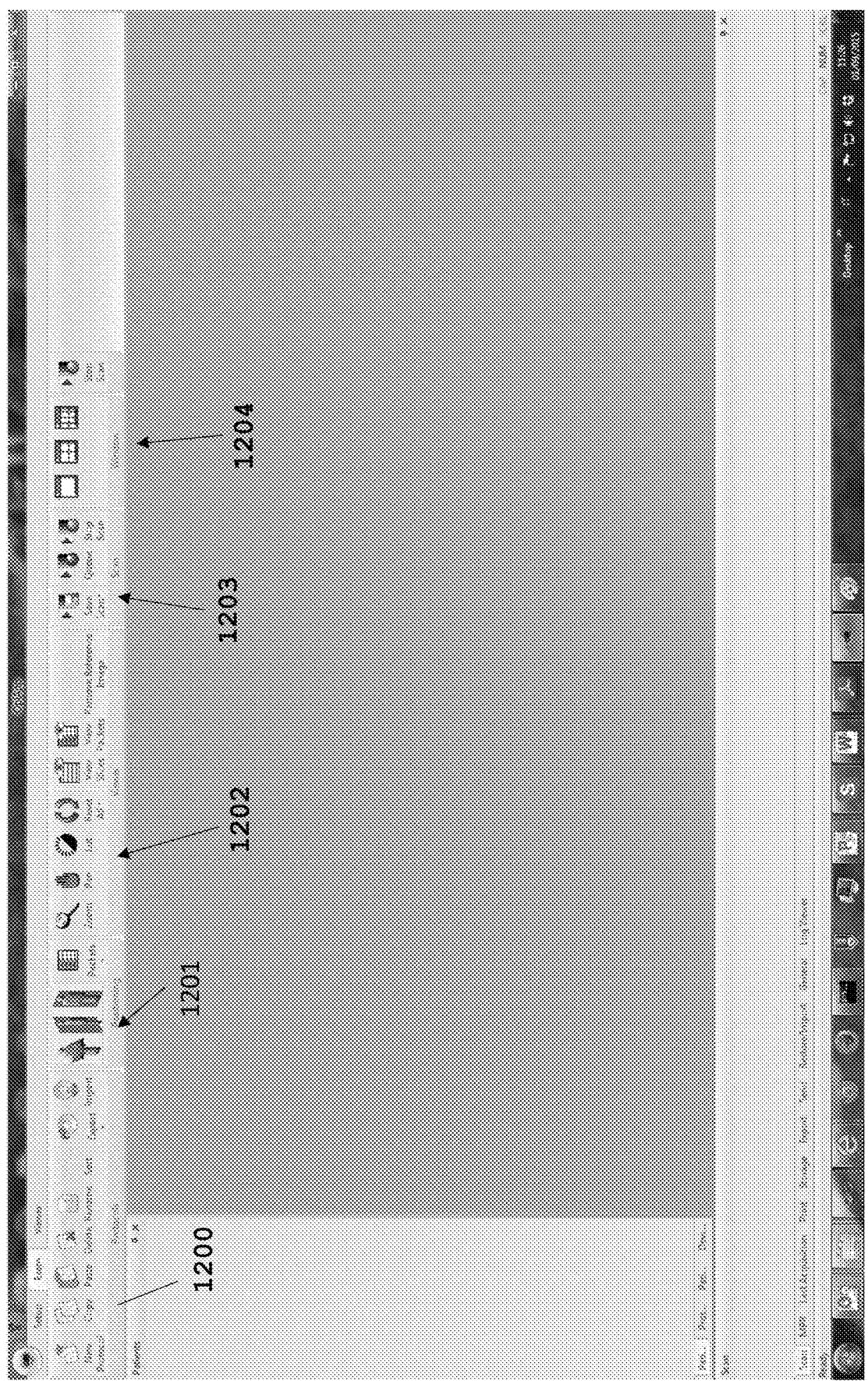
Figure 12A:
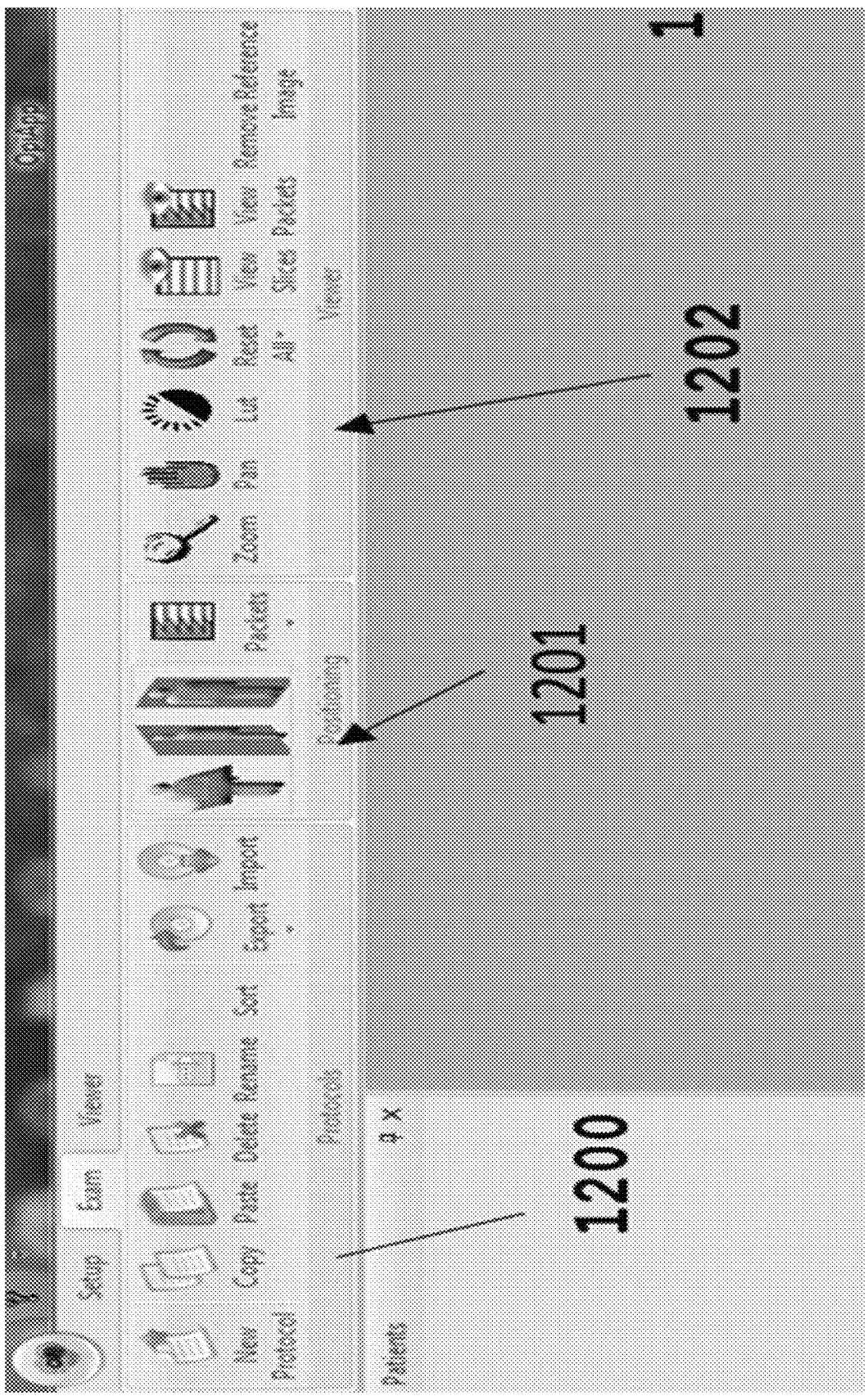
Figure 12B:
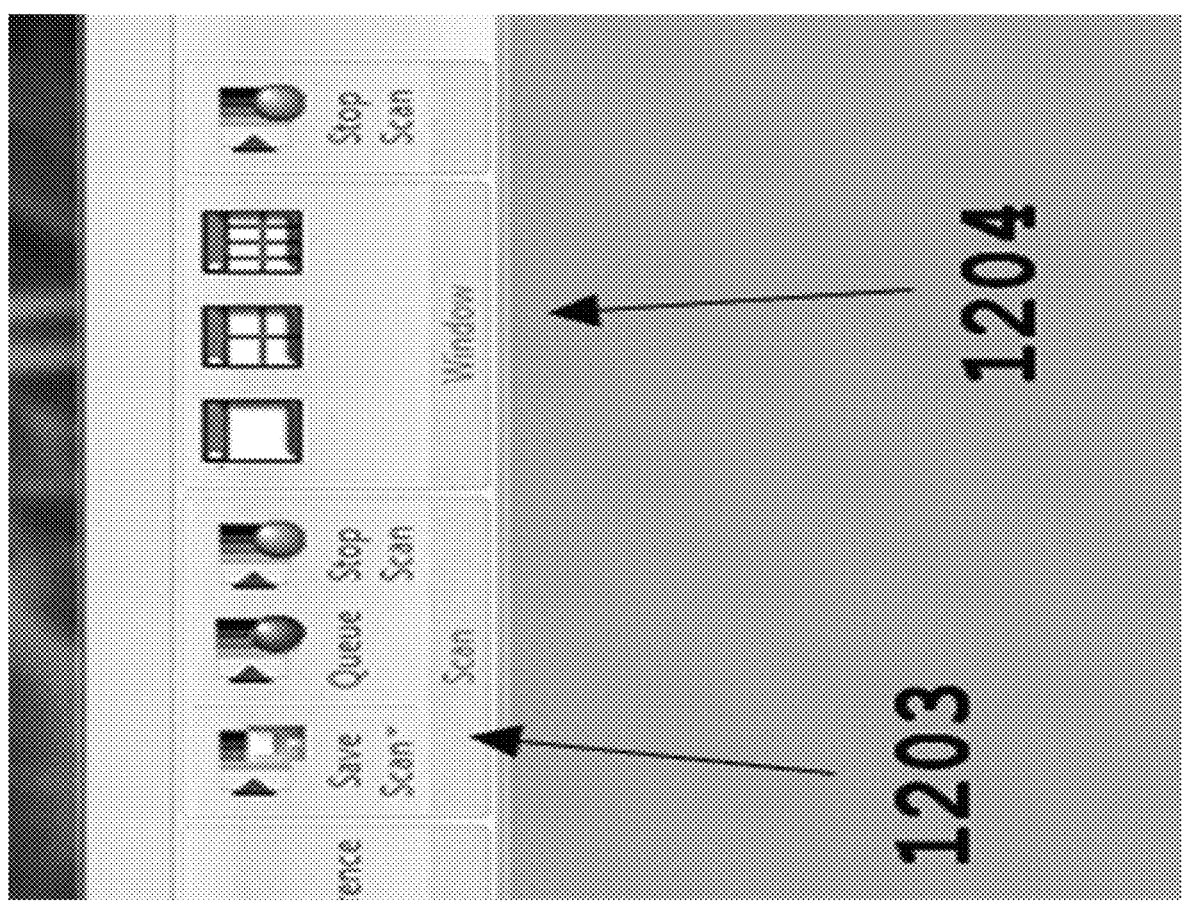
Figure 13:
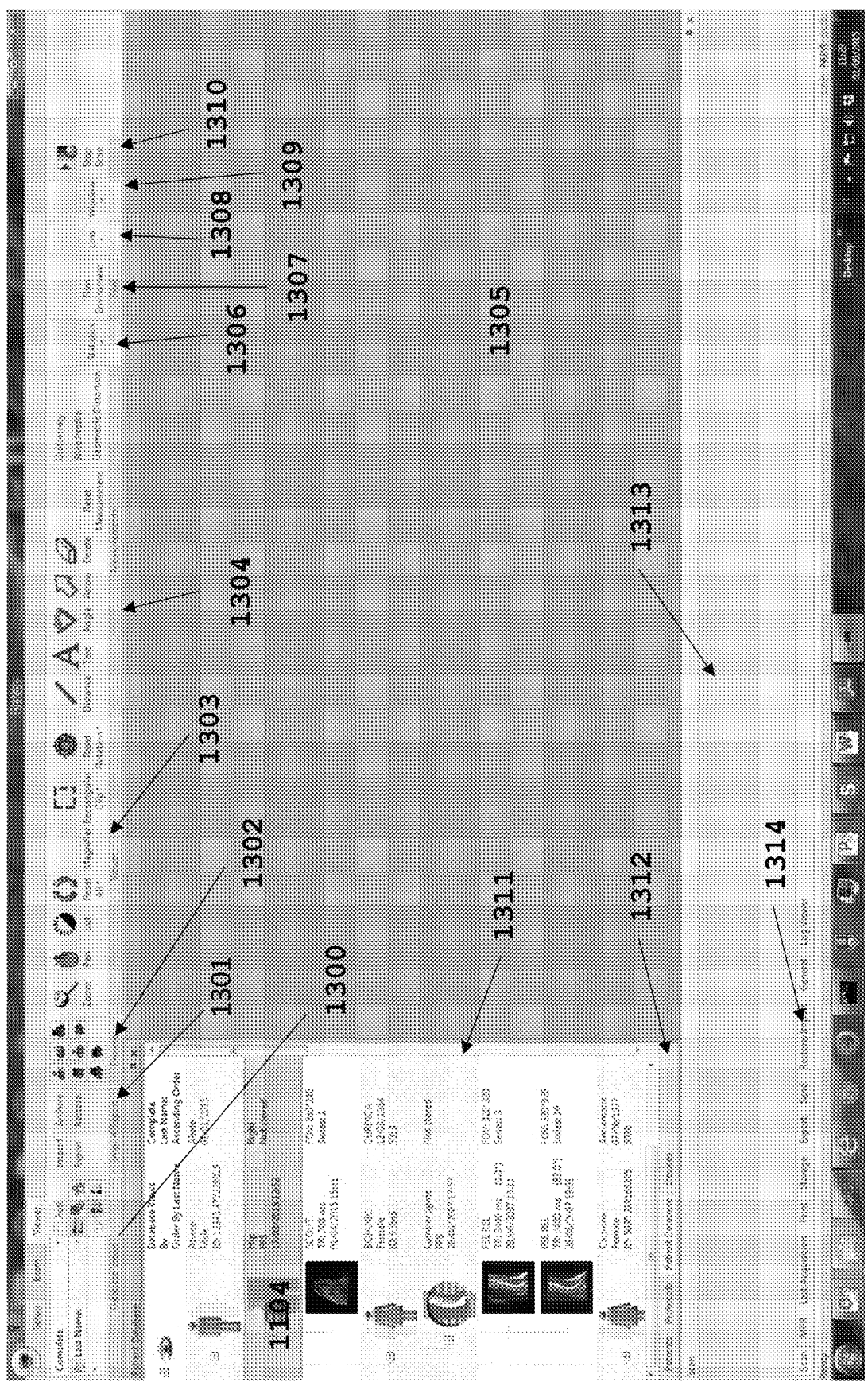
Figure 13A:
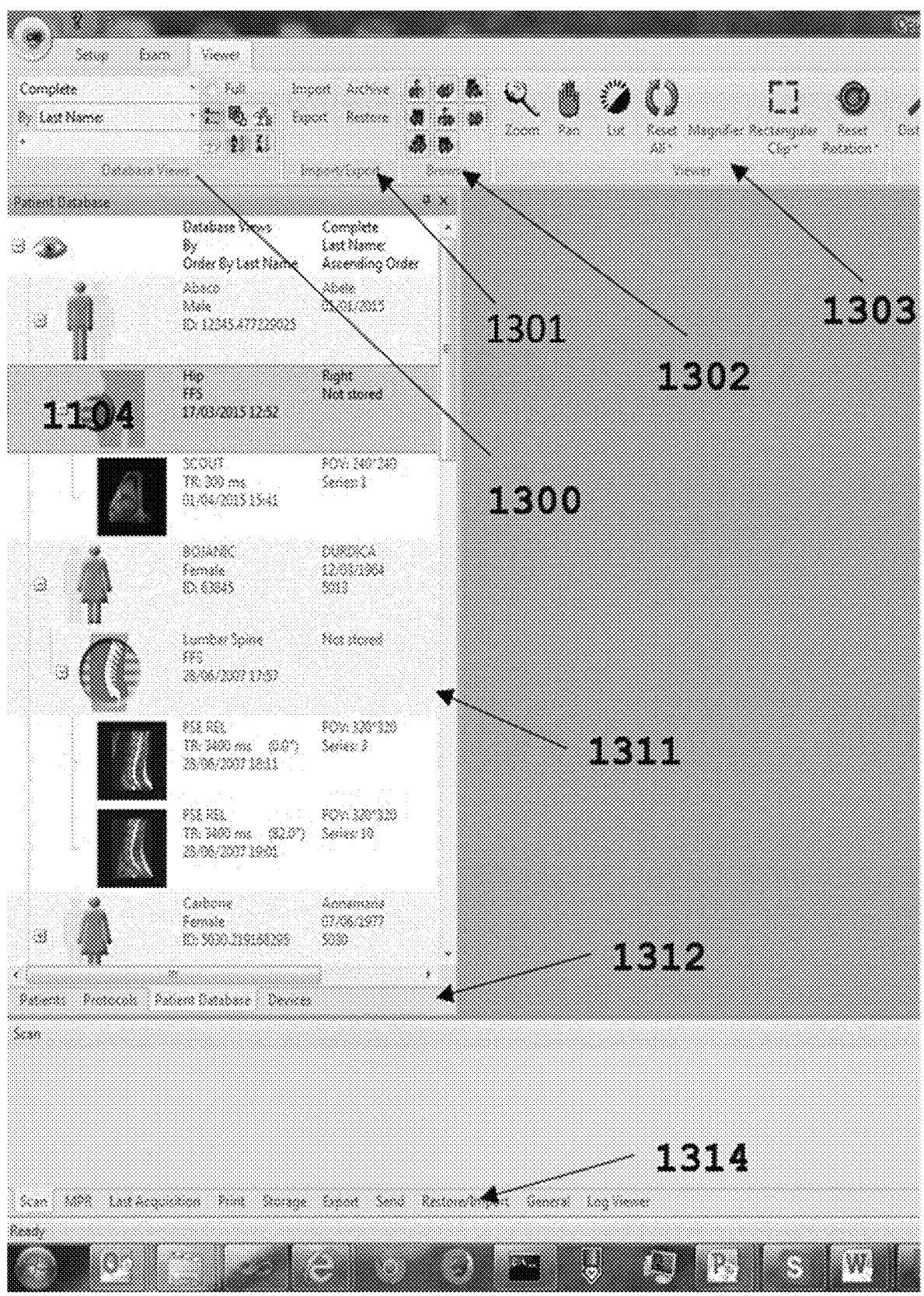
Figure 13B:
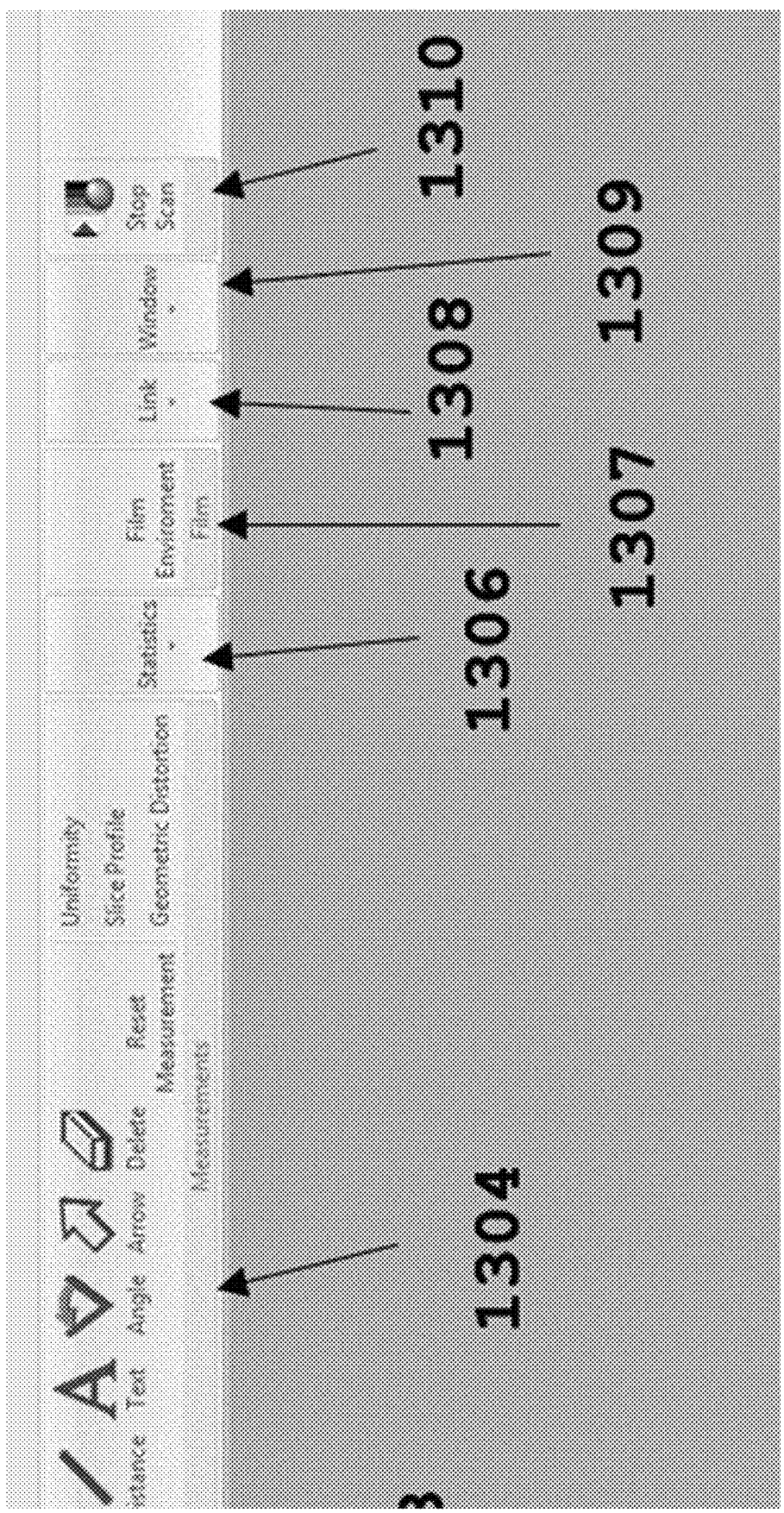
Figure 13C:
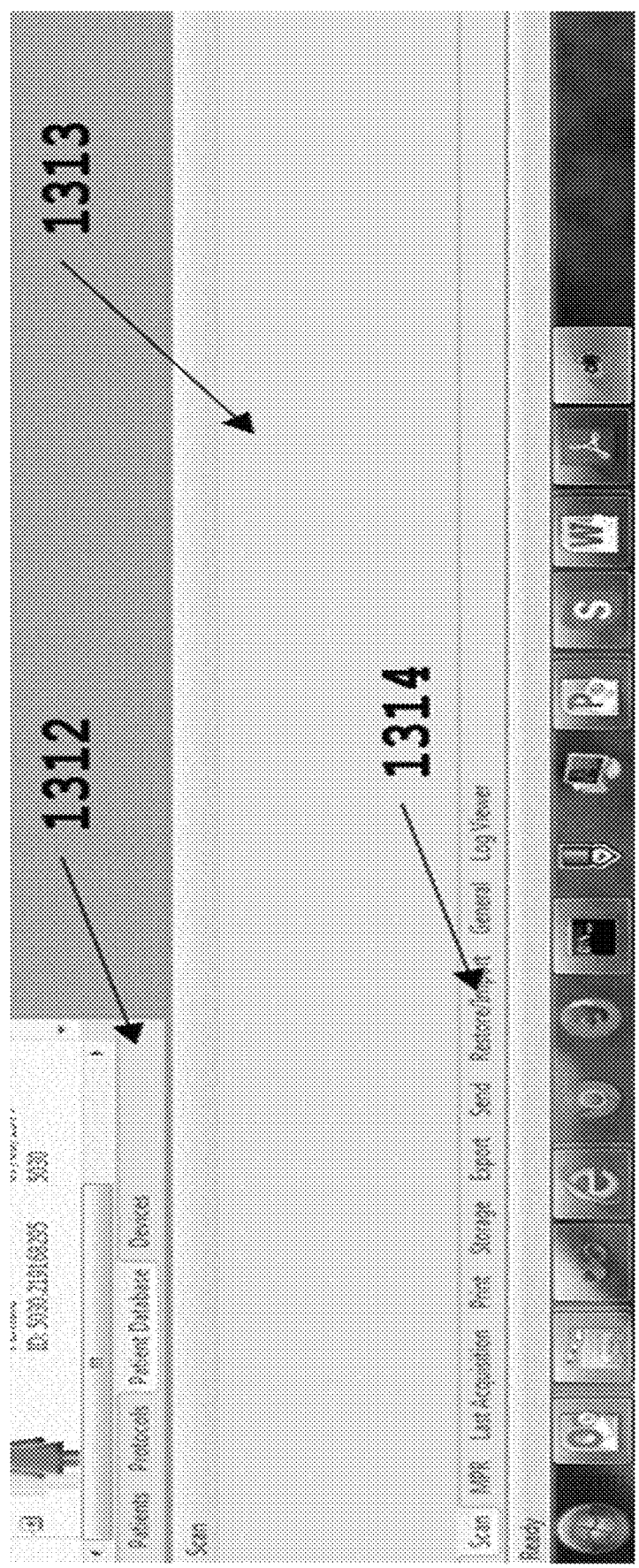

FIGS. 11 to 13 show three screenshots of the graphic user interface displayed on a screen according to an embodiment of the control system for an MRI apparatus. The user interface comprises labels 1100 allowing to carry out setup tasks, the image acquisition process indicated by the label Exam and file content or image viewer.

Each operation label 1100 when selected and activated changes the configuration of the display area and of the tool and ribbon bars 1101 at the upper side of the display region 1103. A lateral display region 1104 and a lower display field 1105 are also provided.

In the setup ambient the tool and the ribbon bars comprises context related buttons and menus 1107 which are grouped according to their functions. A New patient button 1108 starts the process for inputting new patient personal data and the control system generates the corresponding record in the database and the corresponding folder and file in the file system. Existing patients managing tools are provided. In the Get group 1109 different searching tools and or searching key data are provided. Other existing patients managing tools are grouped under the bar Patient 1110 and provides for duplication or deletion of a patient. The group 1111 study contains buttons for managing studies. The term study is defined by the DICOM standard and a study groups several examinations. The group 1112 named Acquisition allows to plan, and carry out the imaging process. The group CAD 1113 comprises the buttons for carrying out image processing or CAD processing of the acquired images.

FIG. 12 shows a screen shot of the interface configuration appearing when selecting the label exam. The ribbon and tool bar is changed and the GUI manager of the control logic has combined different buttons, bars and menus which are related to functions needed for carrying out the functions connected with the examination. Similarly to the previous windows, on the upper bar active buttons are grouped according to their function. The group 1200 named protocols allows to generate a new protocol or to manage existing protocols. The group 1201 named positioning comprises active buttons for executing image slice selection of one or more slice or for positioning several image slices grouped in a packet. The group 1202 named viewer comprises active buttons allowing to navigate the images or to carry out functions relating to influencing the appearance on the screen of the image. The group 1203 named scan comprises active buttons for managing the execution of scan processes. The group 1204 named Window comprises active buttons for dividing the visualization area of the images in the window.

FIG. 13 shows the screenshot of the interface windows which appears when the label viewer is selected. Similarly to the previous examples, the viewer label causes the GUI to change. The upper bars contain new buttons which are grouped accordingly to the function. Group 1300 named Database views allows to select different representations of the structure of the database. Group 1301 named Import/Export allows to import or export data. Group 1302 comprises active buttons browsing for selecting different views for browsing the data. The group 1303 comprises buttons which change some features of the viewed data. A group 1304 named Measurement allows to activate and execute measurement activities on an image displayed on screen in the image display area 1305 of the window, Other buttons 1306 to 1310 allow to carry out further functions launching further environments related to the execution and control of the corresponding function such as statistics, Film generating and film processing, Link, Window and Scanning. In the left hand display area 1311 there is displayed the representation of the tree of the file system in which the saved data is organized and which is constructed according to the examples of FIGS. 6 and 7. A lower bar comprising labels indicated with 1312 allows to change the content displayed in this area 1311 for showing different kind of information. The lower display area 1313 allow to display further data relating to the tasks defined in the bar 1314 by the active labels allowing to change the displayed information in this area.

Figure 14:
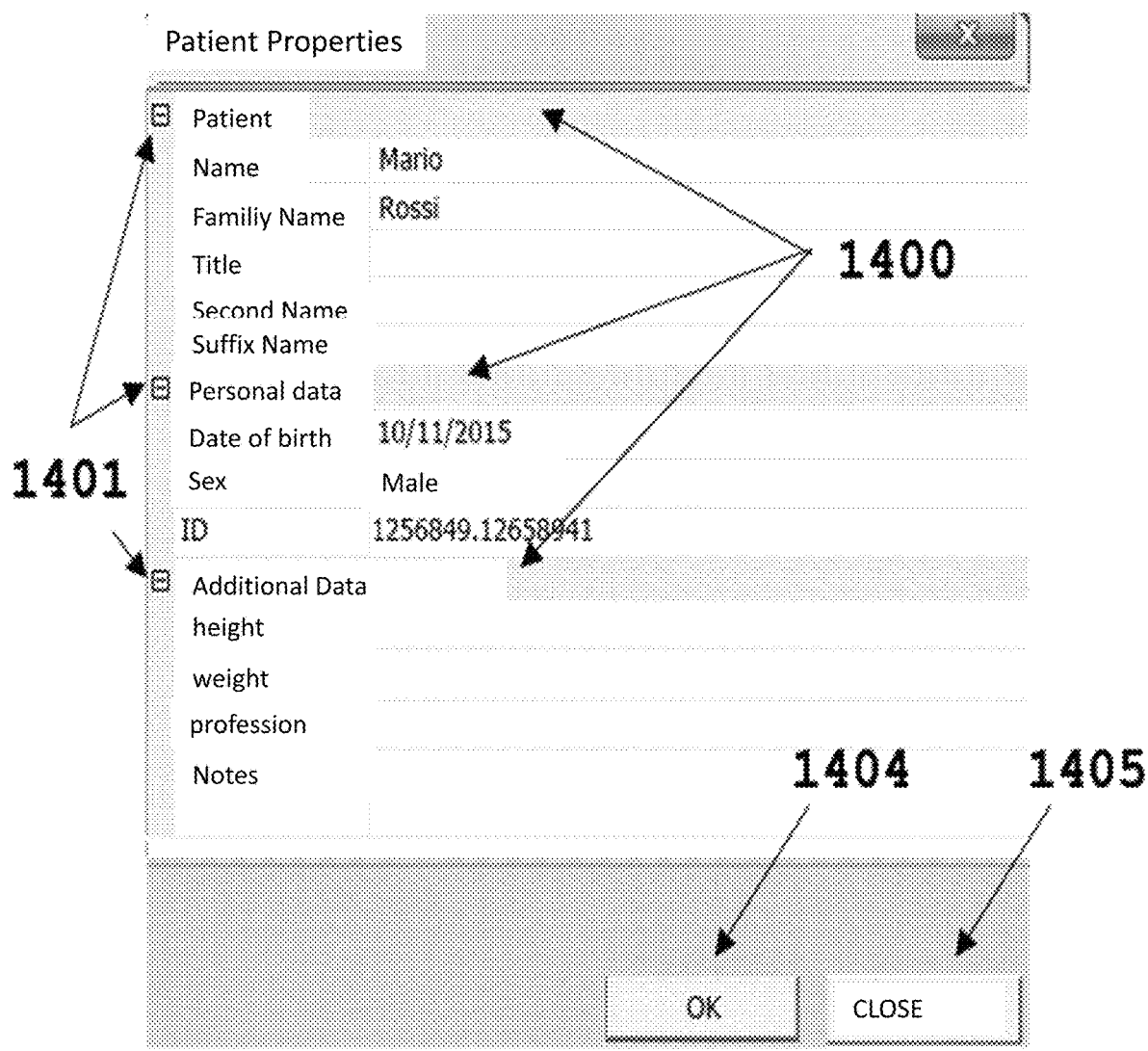
FIGS. 14 to 16 show an embodiment of three data input or selection masks for respectively patient personal data, image series properties, diagnostic study properties.
Figure 15:
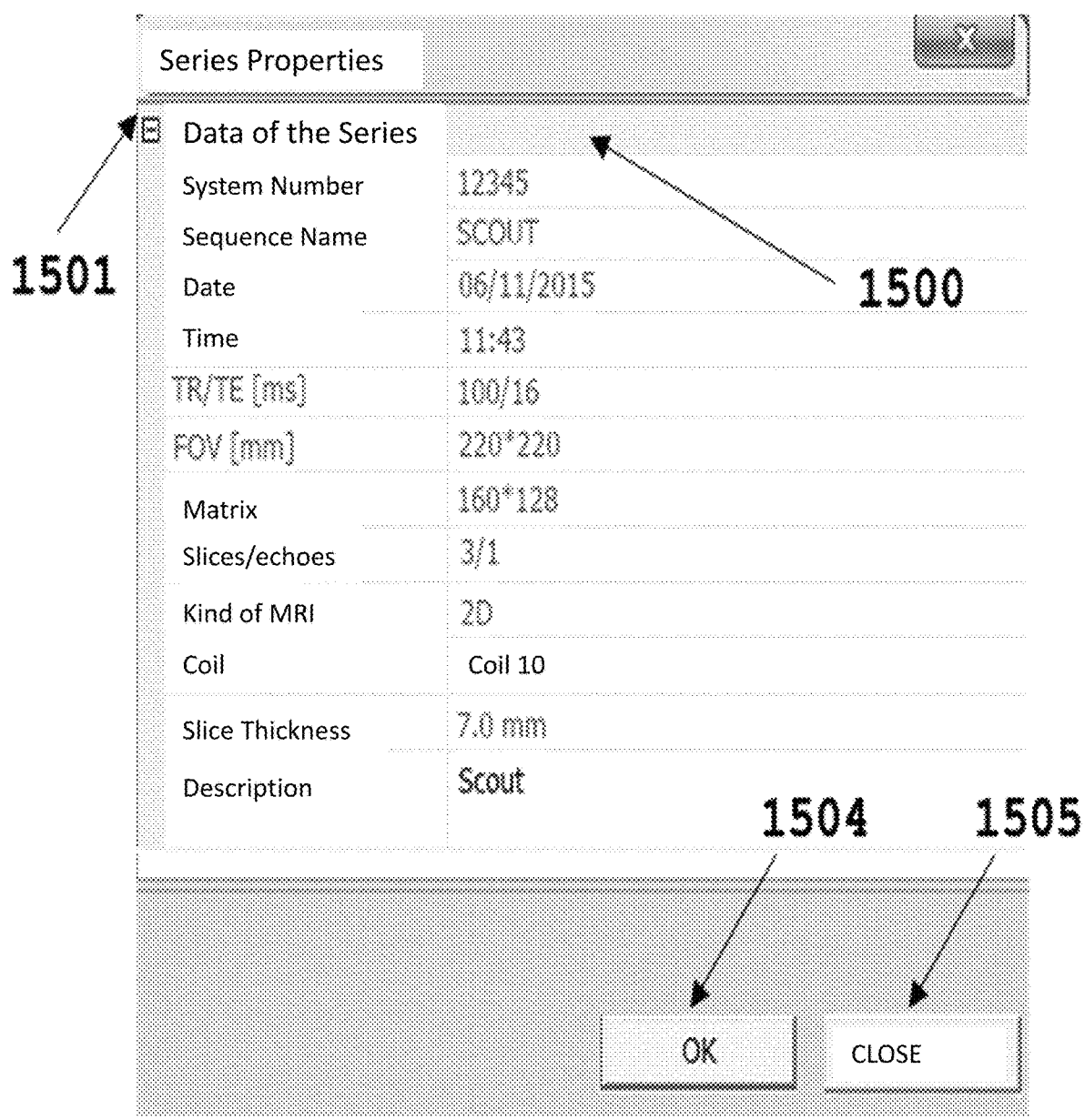
Figure 16:
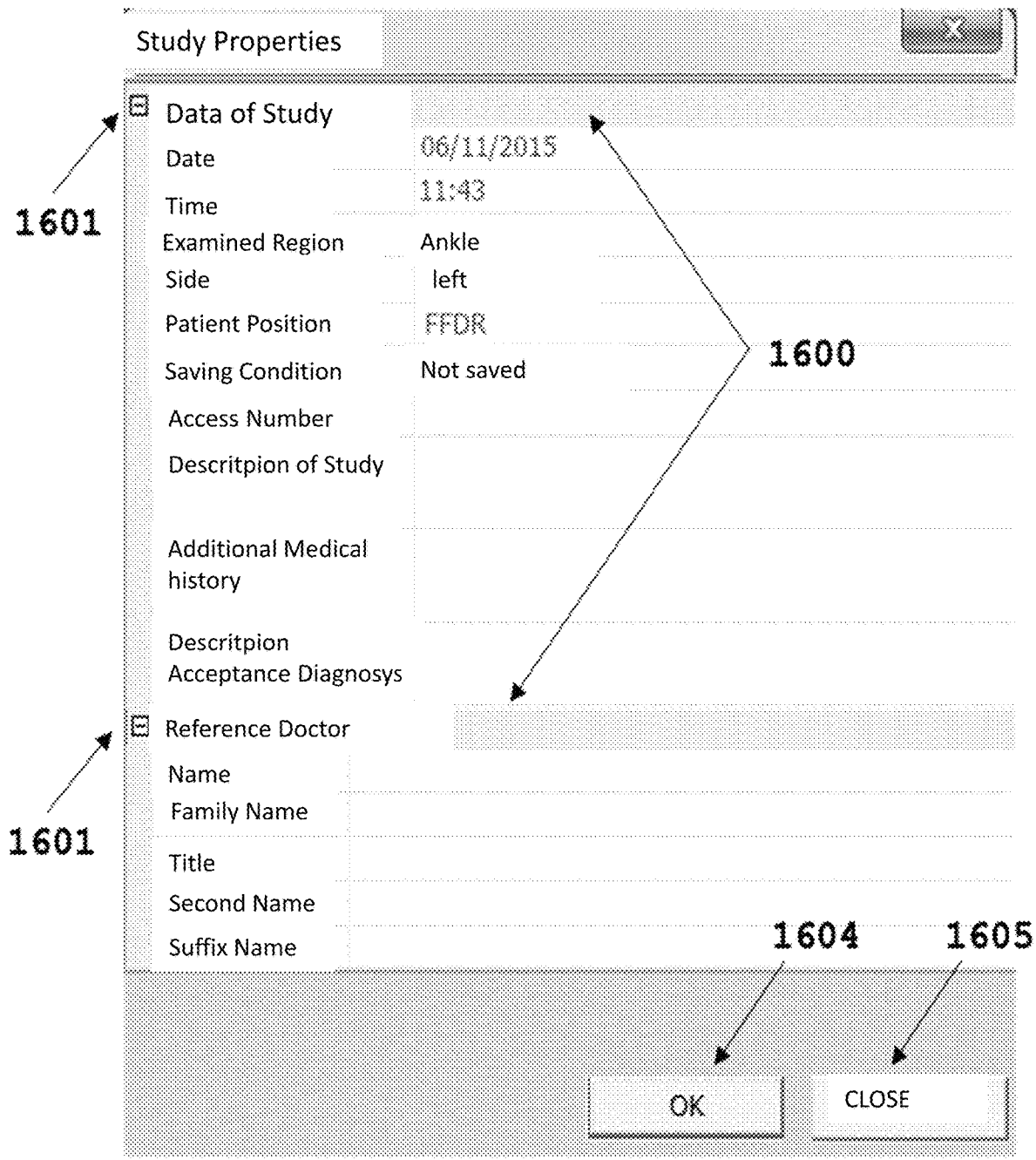

FIGS. 14 to 17 show a different representation of data displayed in the left-hand area for the function relating to the features of the patient, the features of the image series and the features of a study. The data is organized in a table format the subjects 1400, 1500 and 1600 to which the data relates are indicated and the data can be shown or hidden by clicking on a Hide/Show buttons 1401, 1501, 1601 associated to the subject/title 1400, 1500, 1600. The data in each field can be modified deleted or new values can be input. Buttons for saving and closing and for annulation are provided and indicated by 1404, 1405, 1504, 1505, 1604, 1605. This allows to insert or modify data relating to the patient and to task specific features and setting. The interfaces shown in FIGS. 14 to 16 are only some examples of a generic GUI structure which is used for inputting data and setting for several further tasks such as for example scanner settings, protocol configuration, examination configurations, image processing and CAD data and settings.

Figure 17:
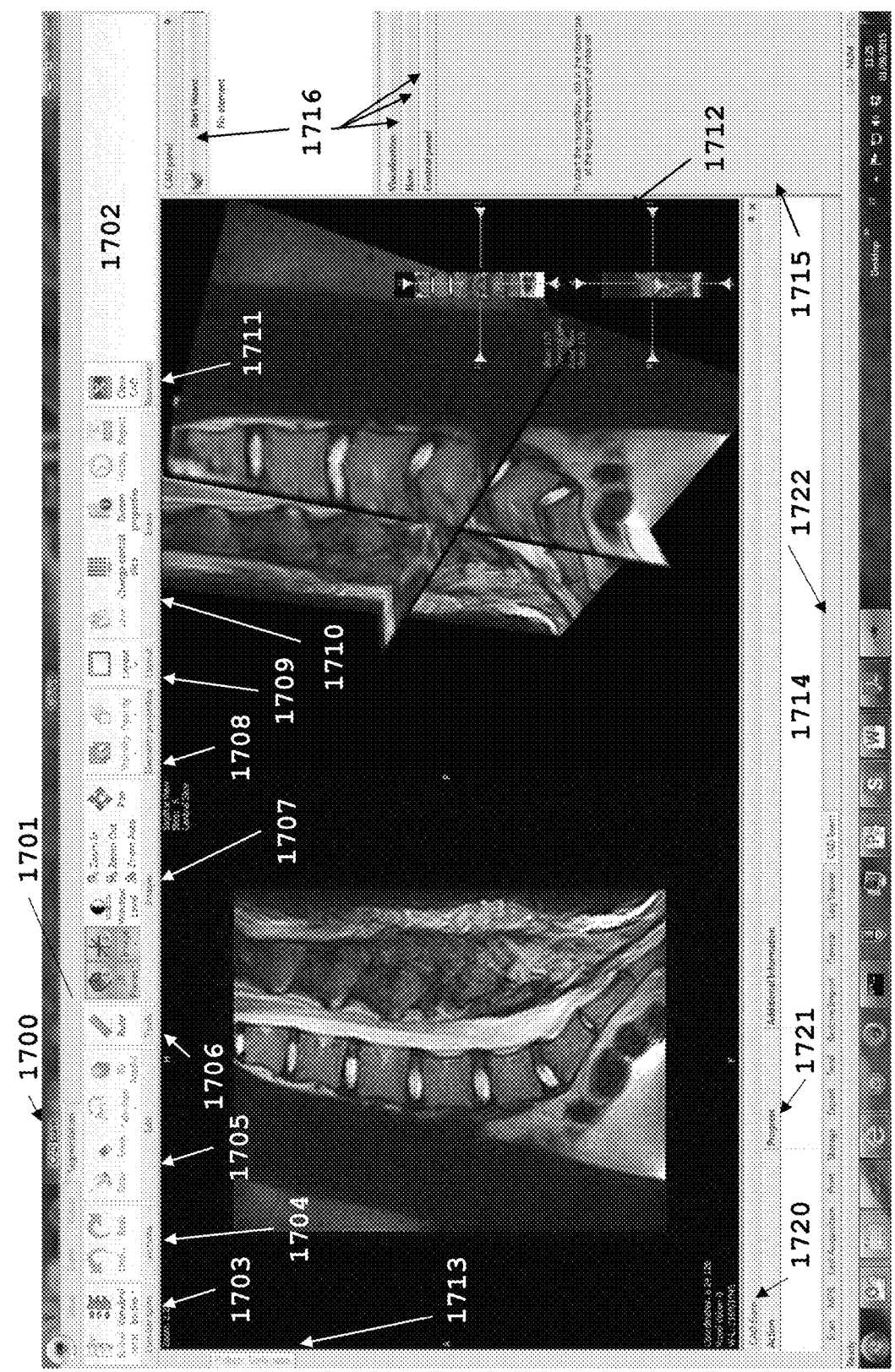
FIGS. 17 to 19 show different windows of an embodiment of the graphic user interface relating to the visualization of different image files and in relation to different functions of the system.
Figure 17A:
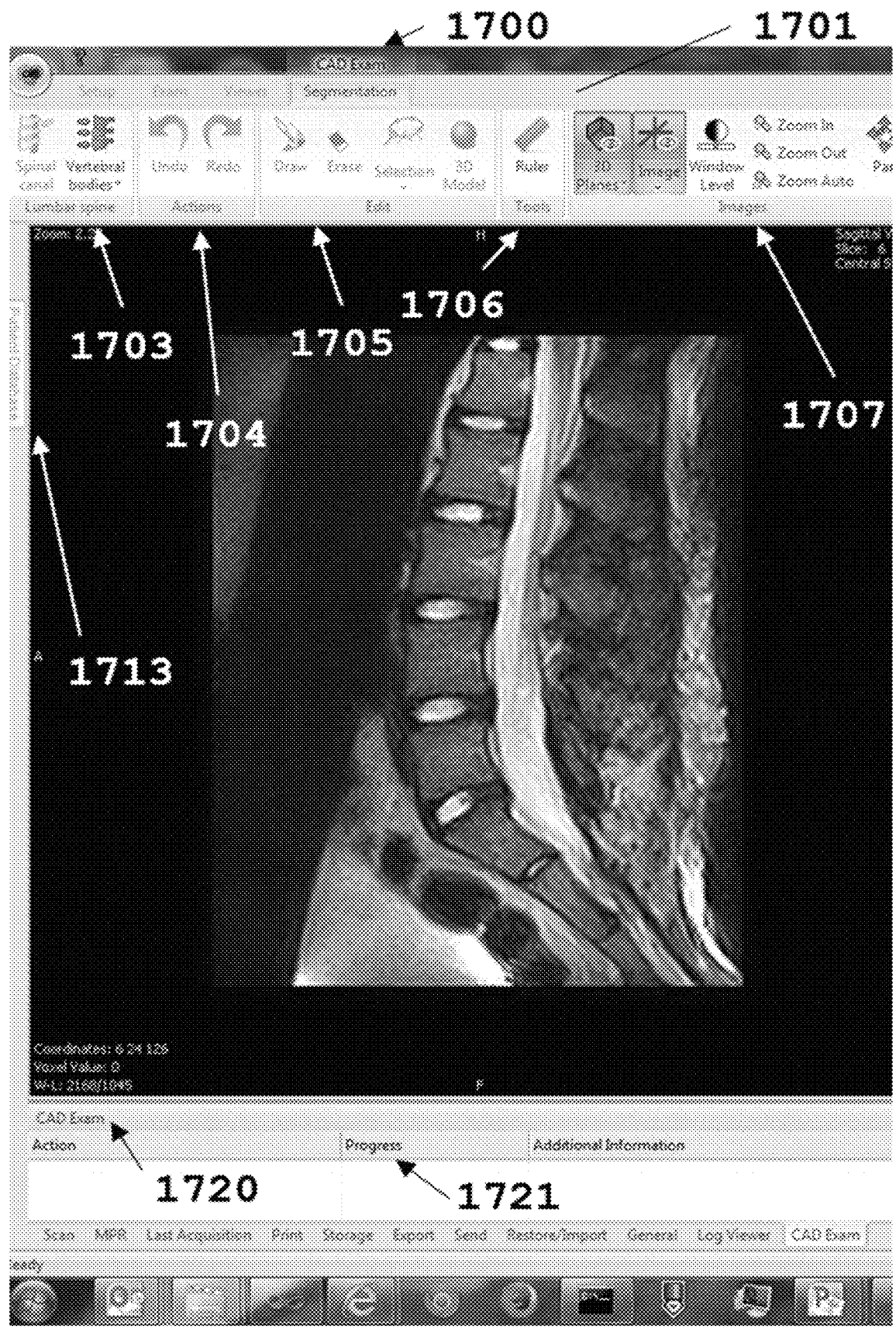
Figure 17B:
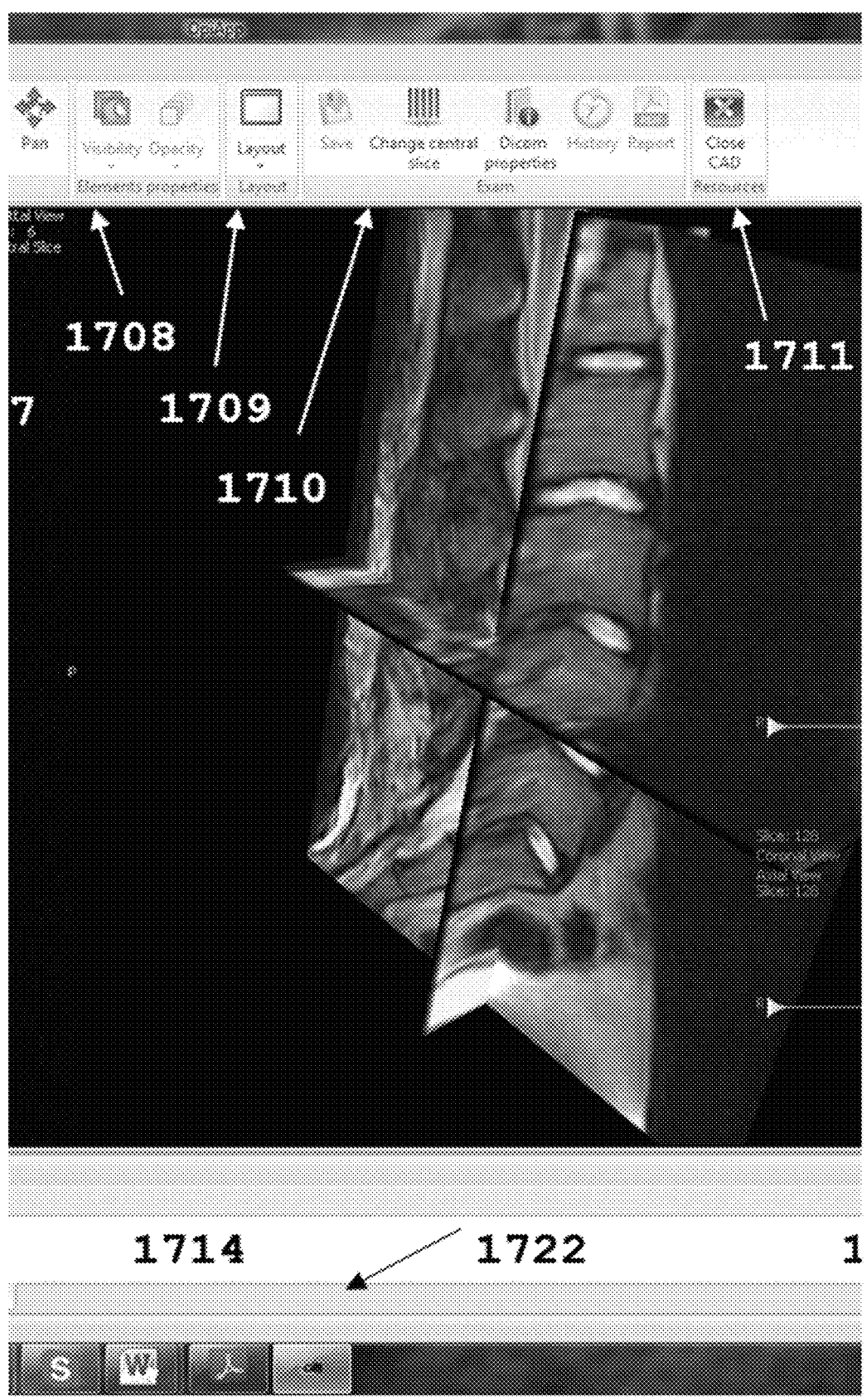
Figure 17C:
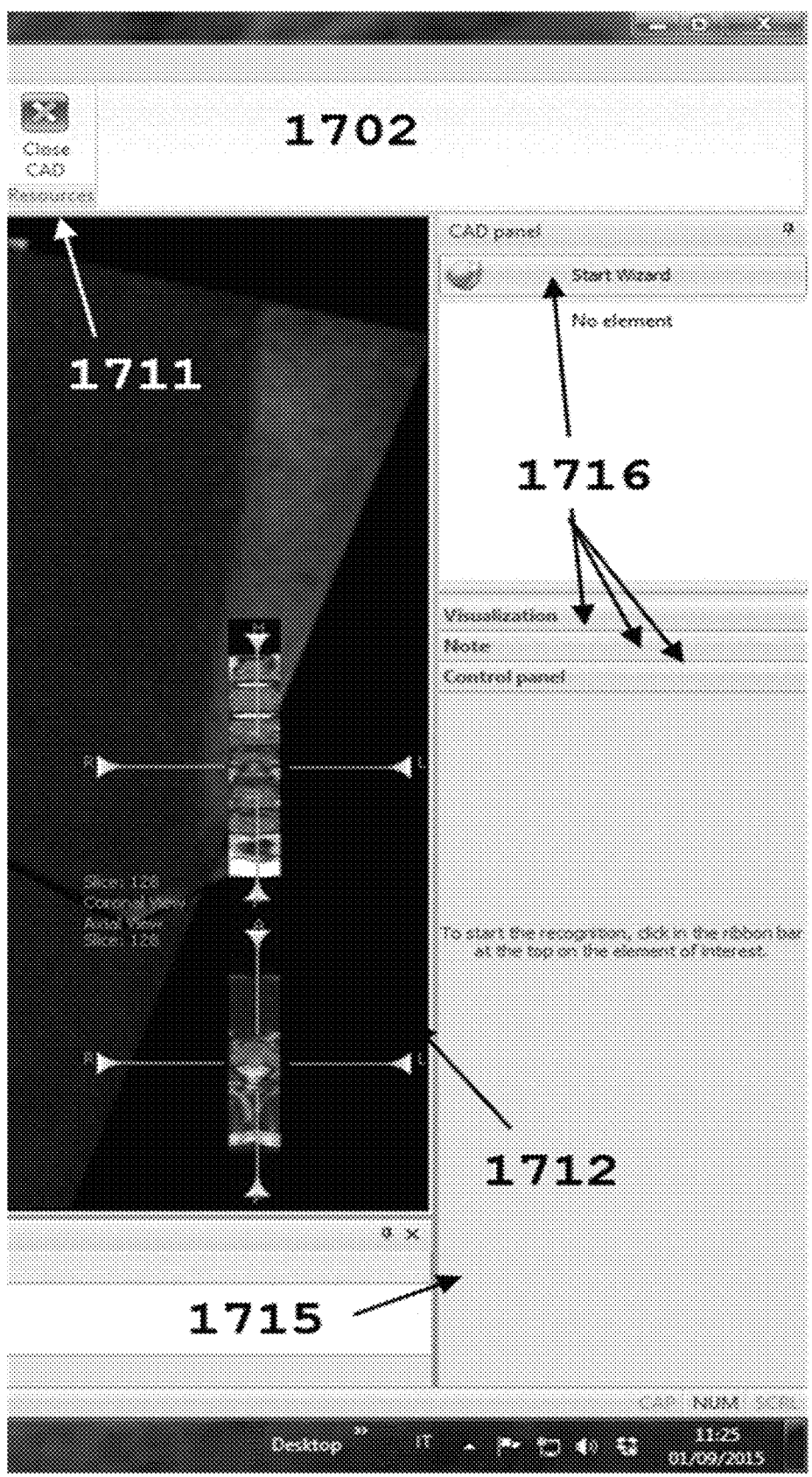
Figure 18:
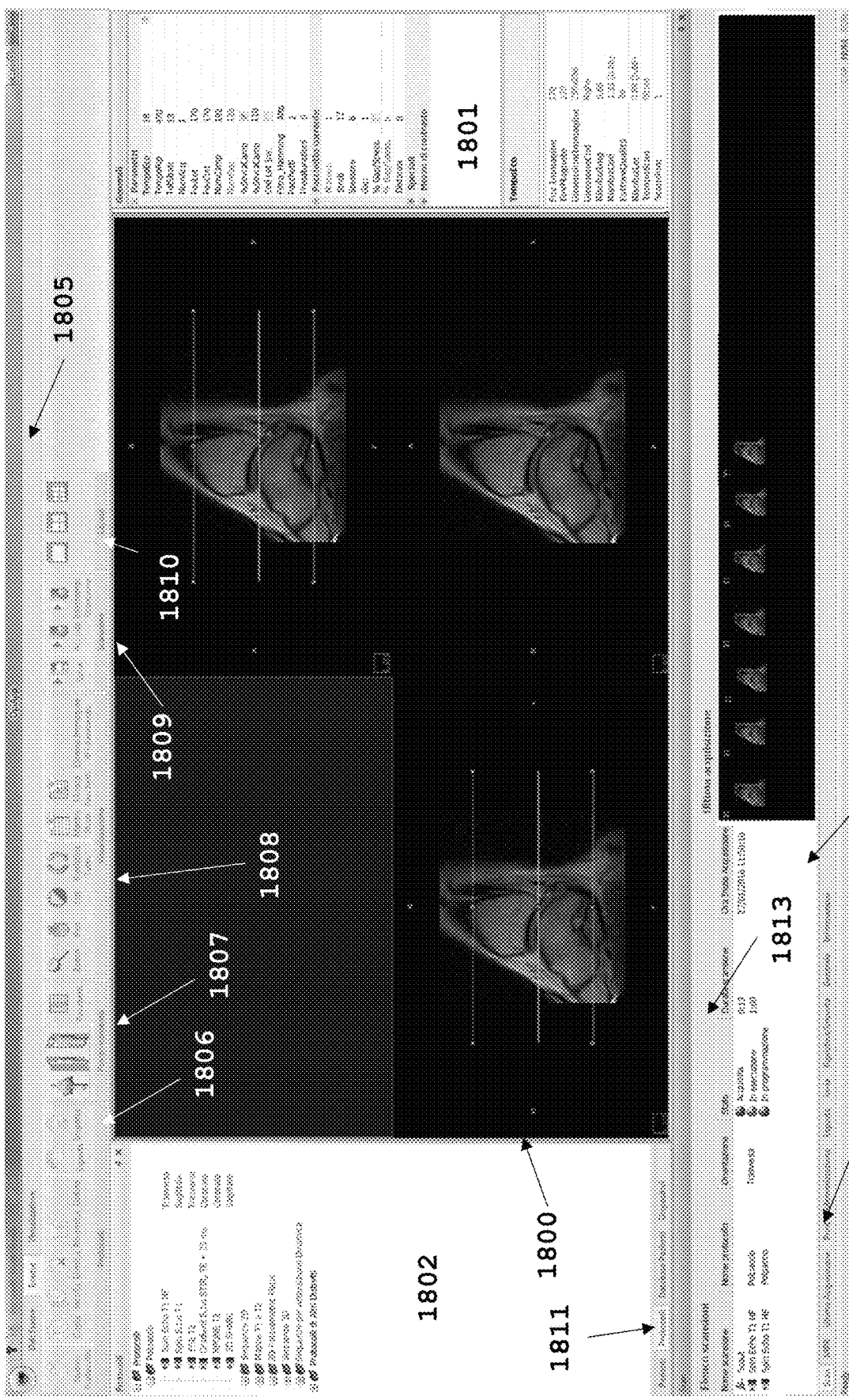
Figure 18A:
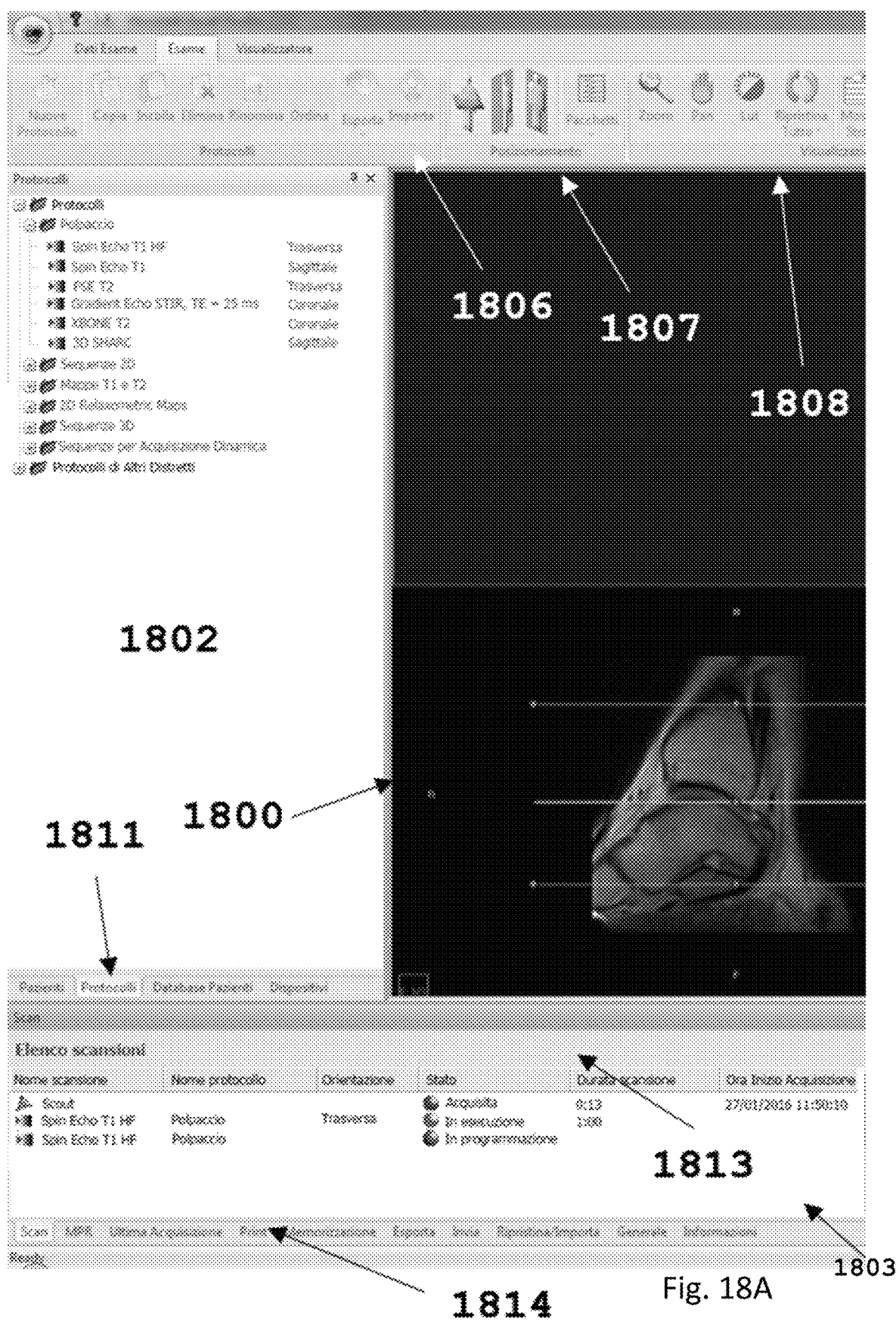
Figure 18B:
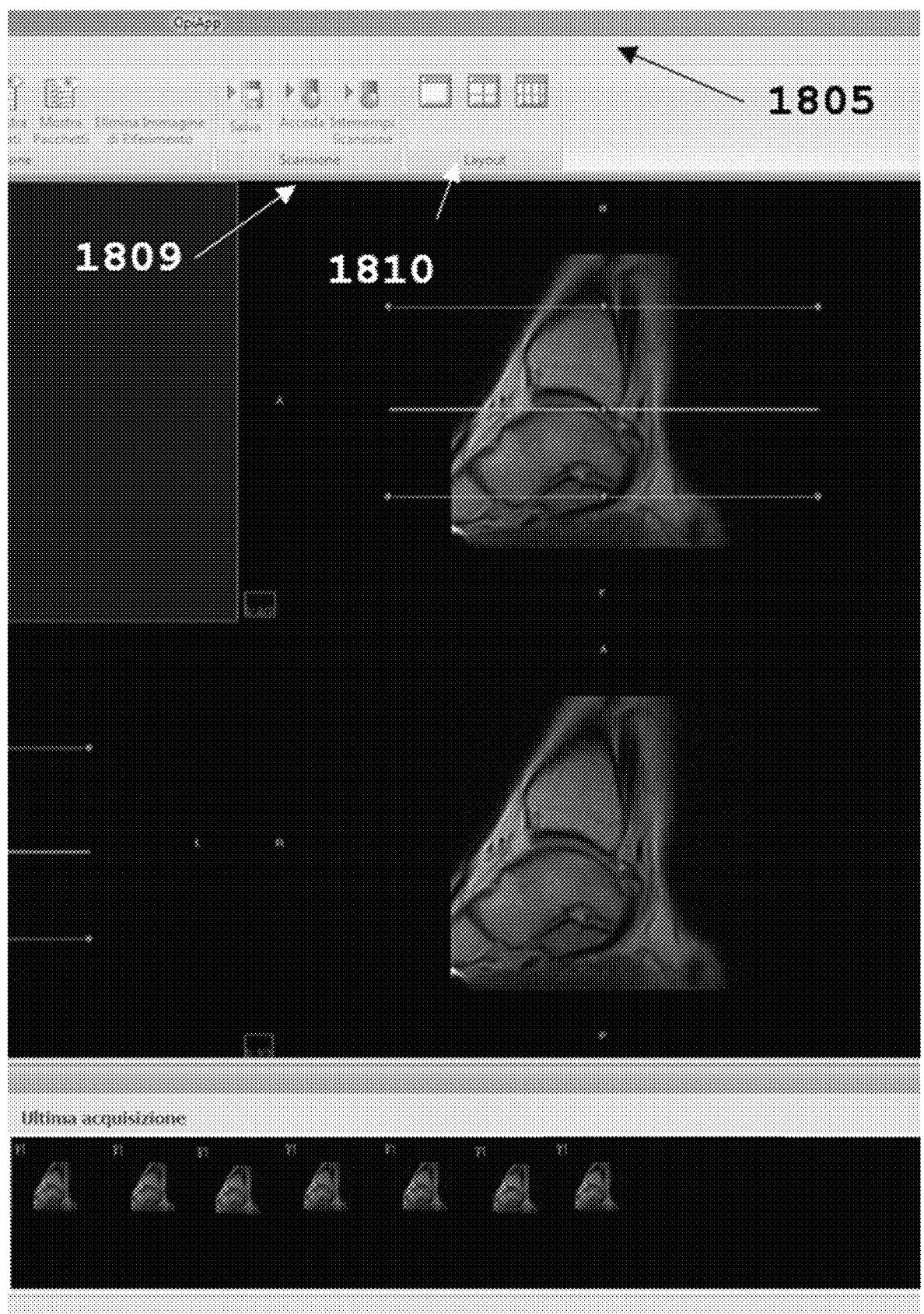
Figure 18C:
Figure 19:
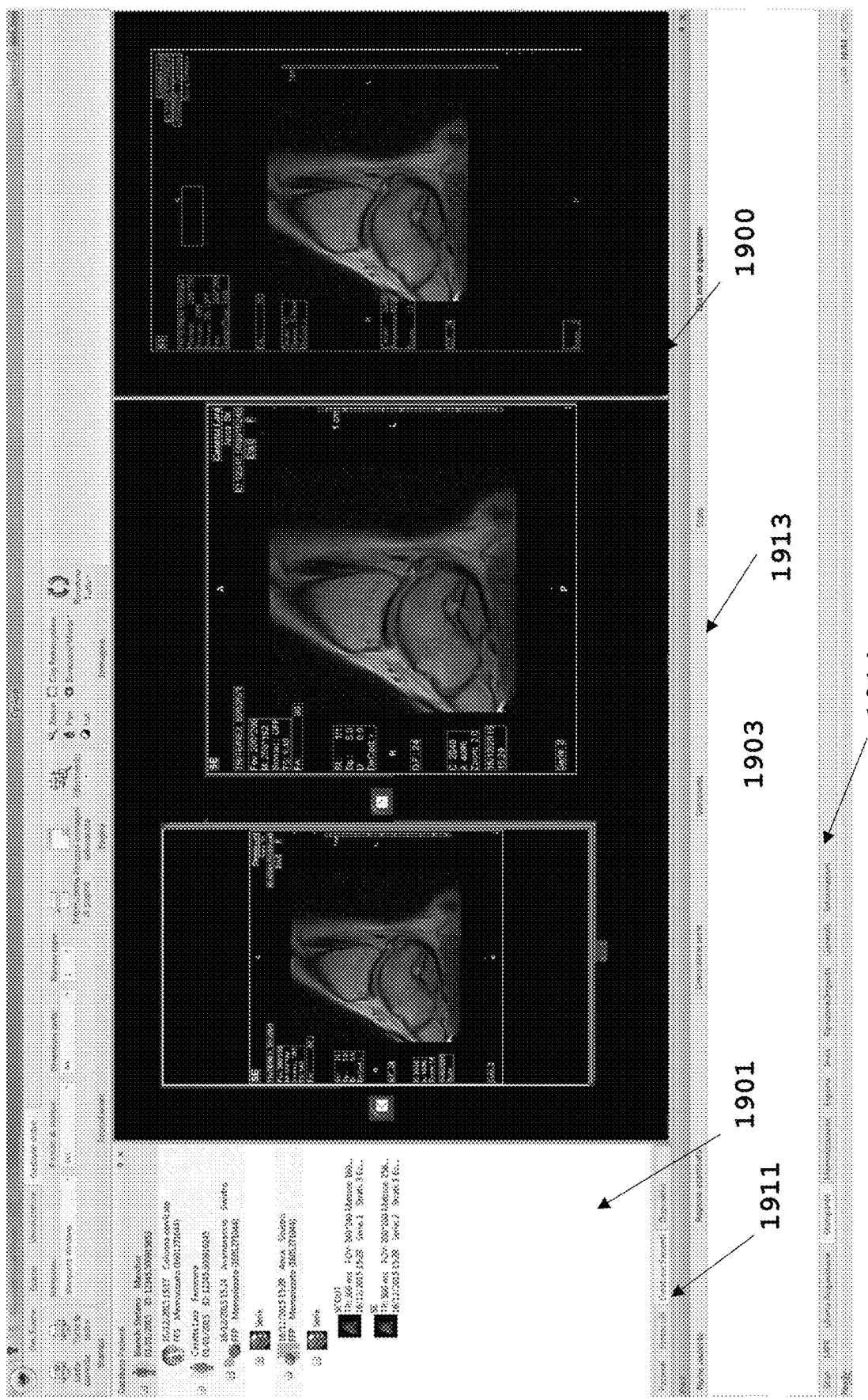
Figure 19A:
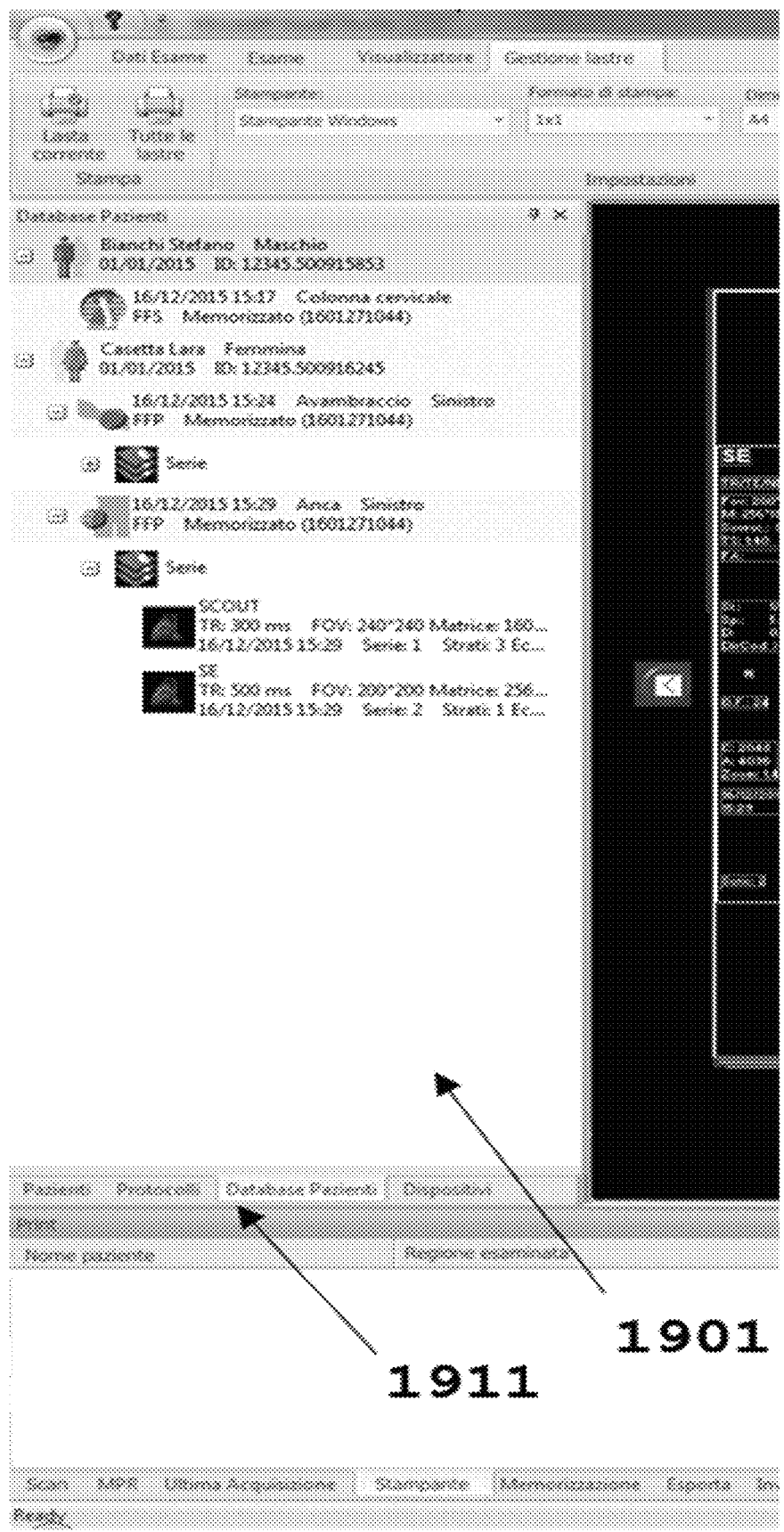
Figure 19C:
Figure 19D:

FIGS. 17 to 19 show further screenshots of the GUI in relation to further examples of the tasks which can be carried out by the control system.

FIG. 17, shows an embodiment of the interface in the CAD examination environment. The environment is signalled by the label 1700. The bar 1701 has further labels for selection further functions and changing the configuration of the interface in relation to the selected function and the tasks connected therewith. In the example of FIG. 17 the function activated is the Segmentation. The bar 1702 comprises active buttons which are grouped according to their functions and which are differentiated by icons representing the function or subject and/or by titles indicating the function or the subject. The examination is directed to the spine and the group 1703 comprises buttons which allows to focus on different anatomical objects of the spine. Group 1704 comprises undo and redo buttons in order to cancel or restore an action carried out on an image. Group 1705 name edit allows to edit actions carried out on the images, group 1706 comprises active buttons launching different tools. Group 1707 named Images comprises buttons relating to change the view of the images. Groups 1708 comprises a group relating to the properties of the elements. Different layout settings can be chosen by the active button of group 1709 named layout. Group 1710 comprises buttons related to the examination and group 1711 resources comprises buttons for closing the cad operation. The display area 1712 shows two images. The left-hand display area for the tree is hidden but it can be shown by clicking on the label 1713 allowing to view again the patient database in the form of a file system tree as in FIG. 13. A right-hand display area 1715 and a lower display area 1714 are provided in which further information and active buttons can be displayed. In the right-hand area 1715 the buttons 1716, allow to open visualization areas related to the operations indicated in a title associated to the button. In corresponding display areas in which the area 1715 is divided suggestions can be shown or the data related to the function indicated on the corresponding button.

Similarly, the lower display area 1714 comprises a bar 1720 indicating the environment, and context configured bars 1721, 1722 comprising labels or buttons for selecting the kind of information to be shown in the display area 1715

FIG. 18 shows another example of an embodiment of the GUI windows relating to a different environment. The window is contextualised with the functions and task related to the environment as in the preceding examples. In this case the window shows four display areas. A central one indicated by 1800 where the images are displayed. A right one and a left one 1801 and 1802 which are structured accordingly to the previous examples. A lower area 1803 is similar to the one described in relation to FIG. 17 but configured in a different way at least for some of the tool or label bars. An upper display zone where the tool bars, ribbon bars and labels are displayed. In the upper label bar 1804 the label exam is selected. The ribbon bar 1805 displays the contextualised groups of active buttons 1806, 1807, 1808, 1809, 1810 which are configured according the principles and criteria described in relation to the previous GUI examples. The left-hand display area 1801 is configured similarly to FIG. 13. In this example, the tree representing the database content as a file system structure is selected in relation to the data about the protocols. The specific database is selected by activating the label protocols in the label bar 1811 of the left-hand display area 1802. In FIG. 17 the tree structure shown in this right-hand display area was the one related to the Patient Database, which was selected by activating the corresponding label. In the central display area 1800 is divided in four fields each one showing an image. The group 1807 named Positioning is activated and in the different fields the position of the slices are drawn on the corresponding image of some of the fields. The selected protocol for the selected anatomic district are highlighted in the tree of the left-hand display area 1801. In the right-hand display area 1802 the settings of the acquisition process are shown in a table form according to the configuration and principles described for this display area in relation to the example of FIG. 17 but contextualised in relation to the content with the environment examination. In the lower display area 1803, environment list of scans is activated and the label and tool bars 1813 and 1814 relating to this environment are shown. In the toolbar 1814 the button named scan is selected and in the display field 1815 a table of the different scans, their status and the icons of the acquired images of the last scan are listed.

According to the embodiment of the file path manager and tracker, when clicking on one of the image fields in the central display 1800, the corresponding file in the tree representation in the left-hand display area 1801 is highlighted. The link to the file location in the file system and/or in the database representation is dynamically maintained and shown in the file system and/or database representation, allowing the user to browse the information related to the visualized and selected image in relation to the patient, to the scan process and to image processing results carried out on the said image or other tasks and data related to the image without the need to follow the entire path every time for example by opening the database or file system representation and folder by folder returning to the file for evidencing the relation to the other data related to the visualized file content or for carrying out tasks on the file which content is visualized and selected or on related data.

Activating one of the labels in the bar 1812 the corresponding representation of the file system and or of the database structure is shown indicating for example the patient which is related to the file which image is selected on the central display area 1800 to which the image is related and all the other data in the folders or subdirectories to which the file of the selected image is related or in which the folder containing the said file or the said file are allocated.

FIG. 19 is a further example of a screenshot of a GUI windows relating to the environment Image manager as it is activated by the corresponding label in the bar in the upper display area 1904. In the central display area 1900 which is divided into two display fields positioned one beside the other two images are visualized. In the left-hand display area 1901 the database tree is represented and the folder sequence is open starting from the patient folder down to the last nested folder where the image files are allocated. In this example—the label Patient Database is activated in the lower bar 1911 of the left-hand display area 1901. The right-hand display area is hidden.

The lower display area 1903 the function print is selected in the bar 1913 and in the lower bar 1914 the device printer is selected. A table for listing the different images and/or data to be printed and comprising information on the printing process status is visualized and in the present example since there is no print command active no file is listed in the table.

Figure 20:
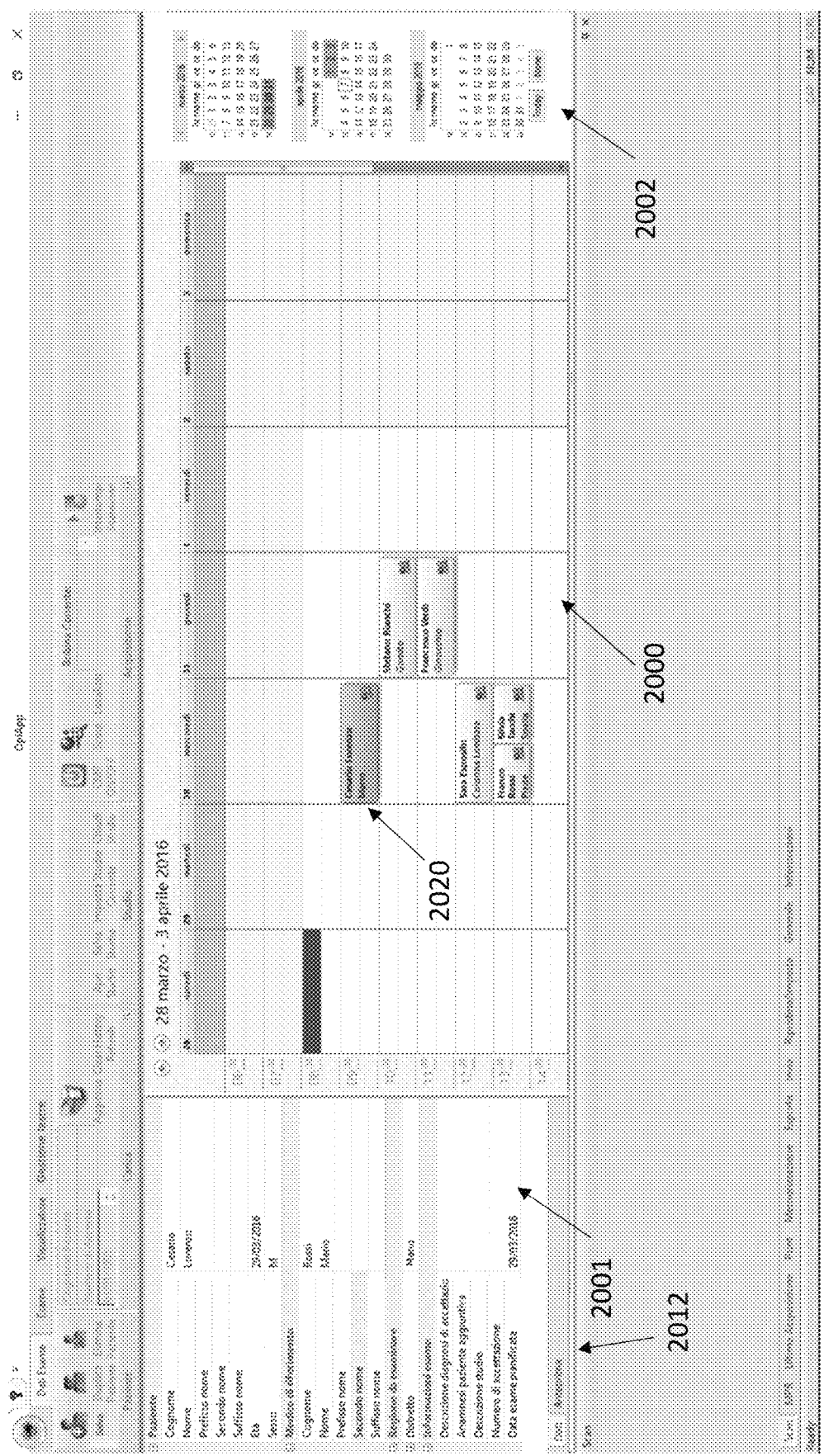
FIGS. 20 and 21 show two different screens of the user interface relating to the scheduler of the control system for scheduling the examination activities.
Figure 20A:
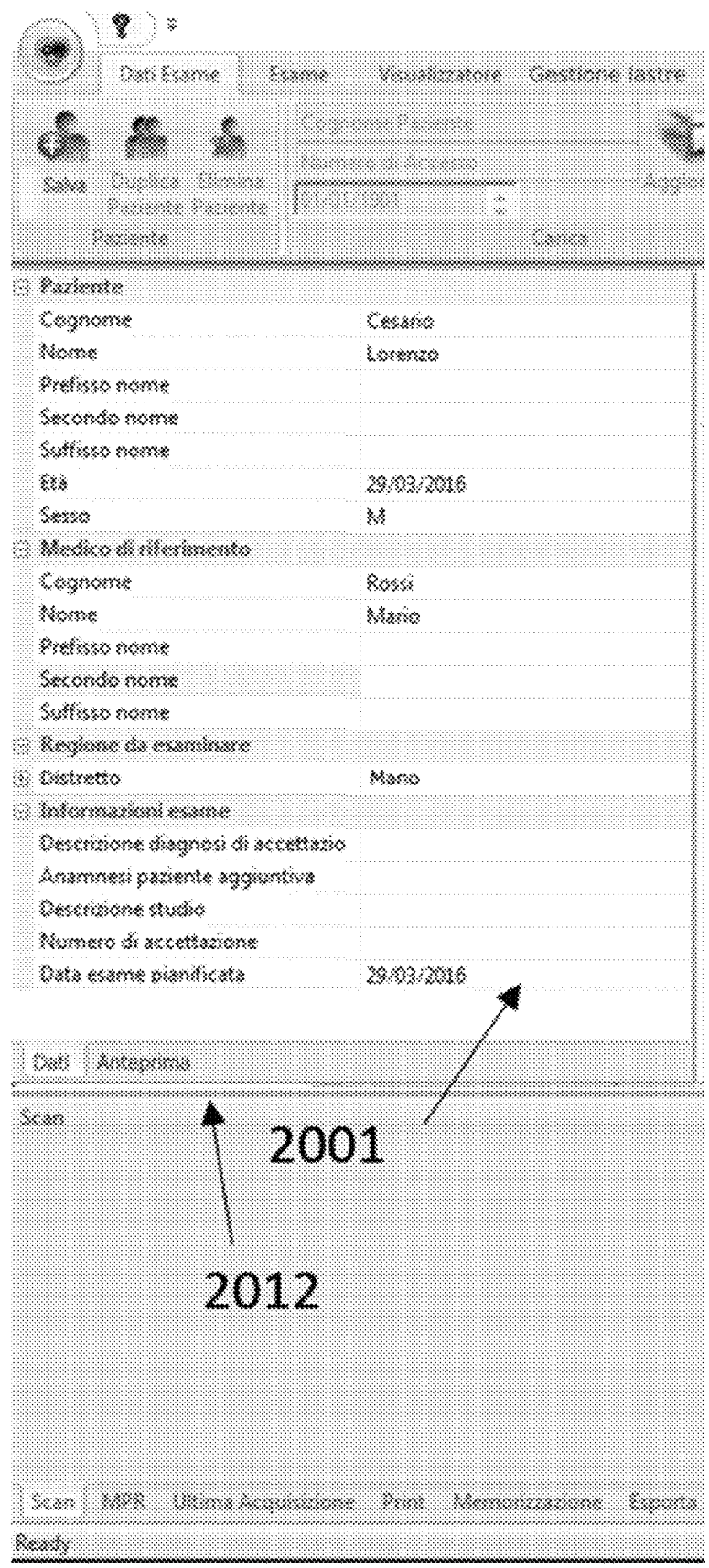
FIGS. 20A to 20C and 21A to 21C are enlarged views of FIGS. 20 and 21.
Figure 20B:
Figure 20C:
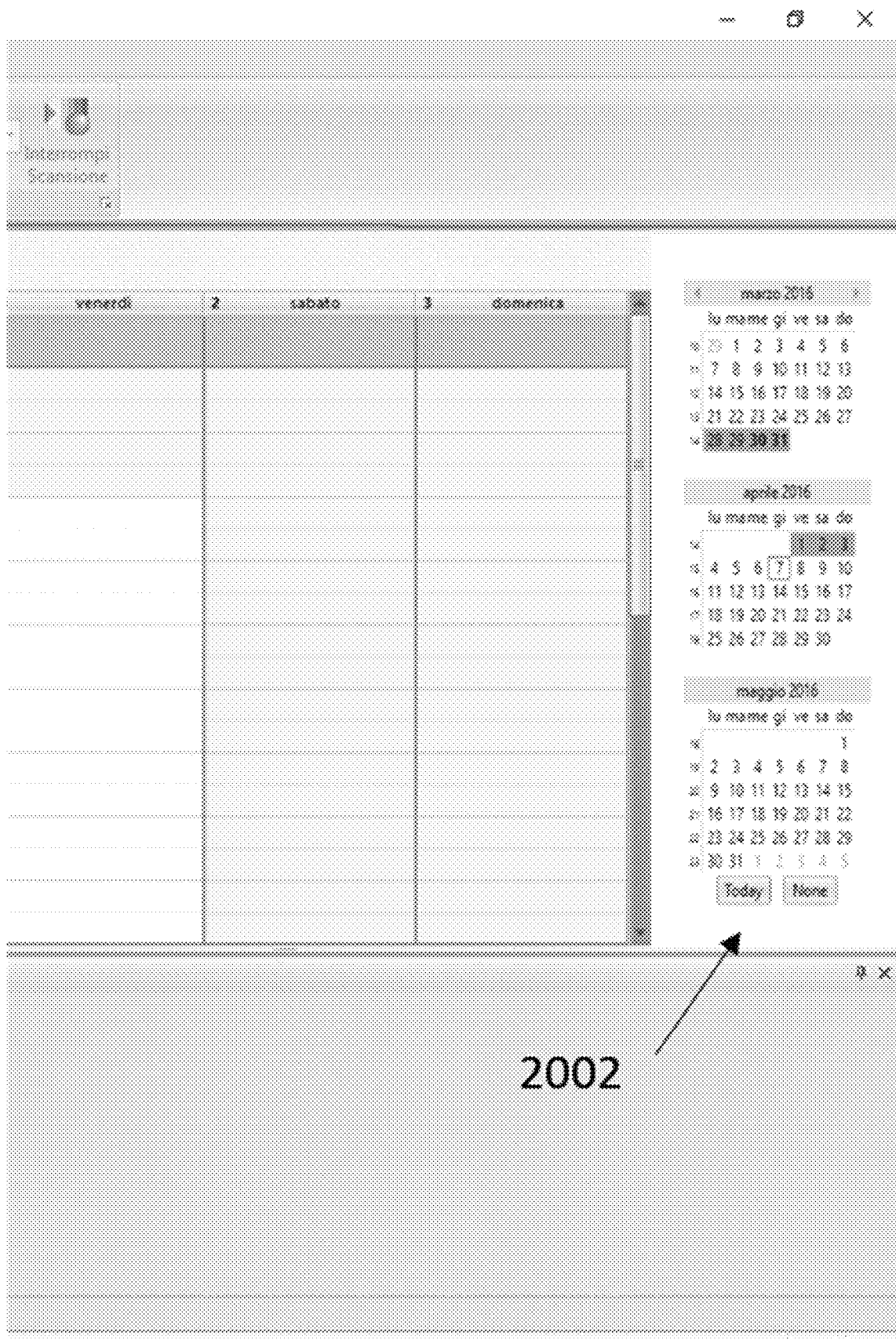
Figure 21:
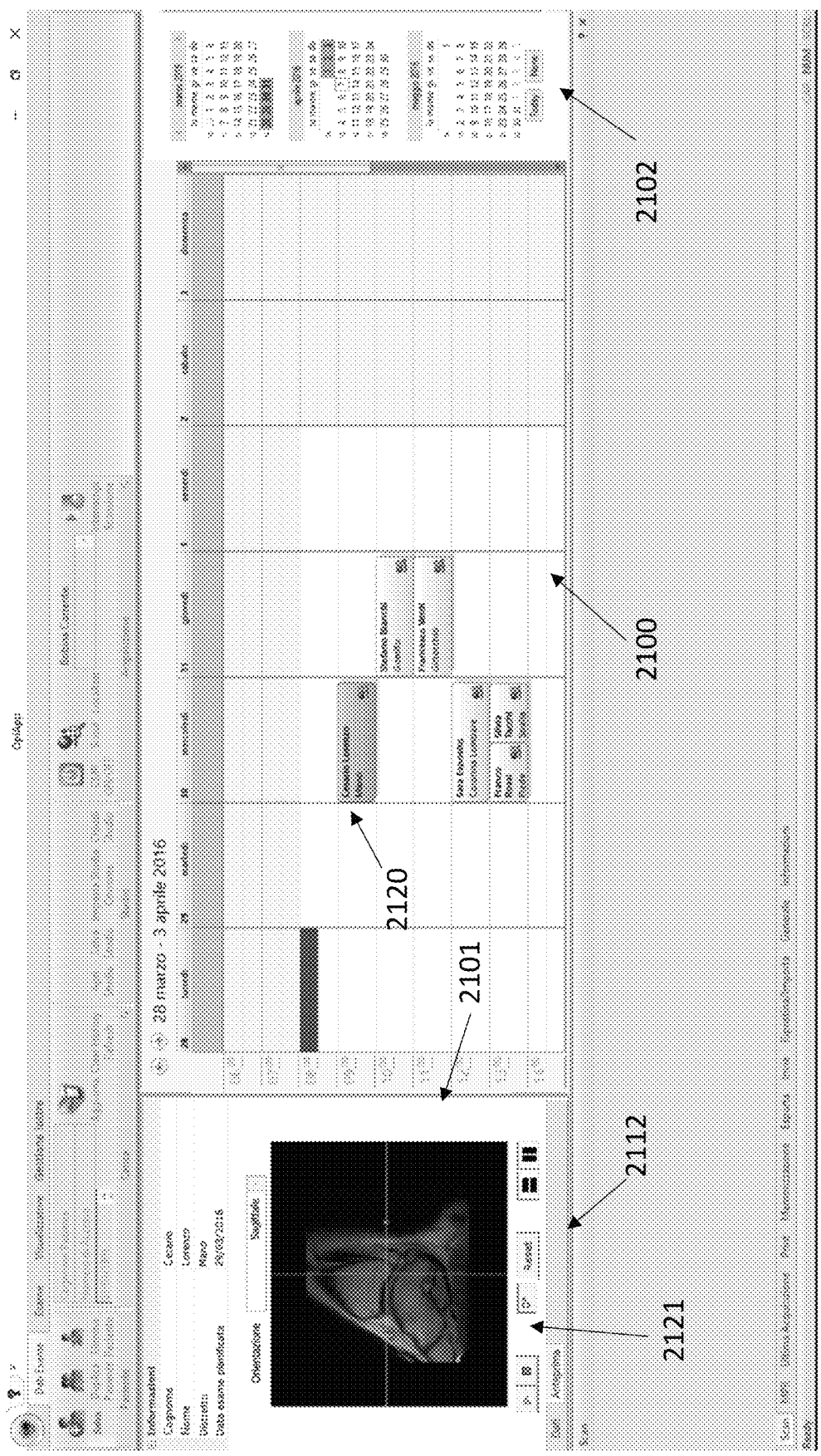
Figure 21A:
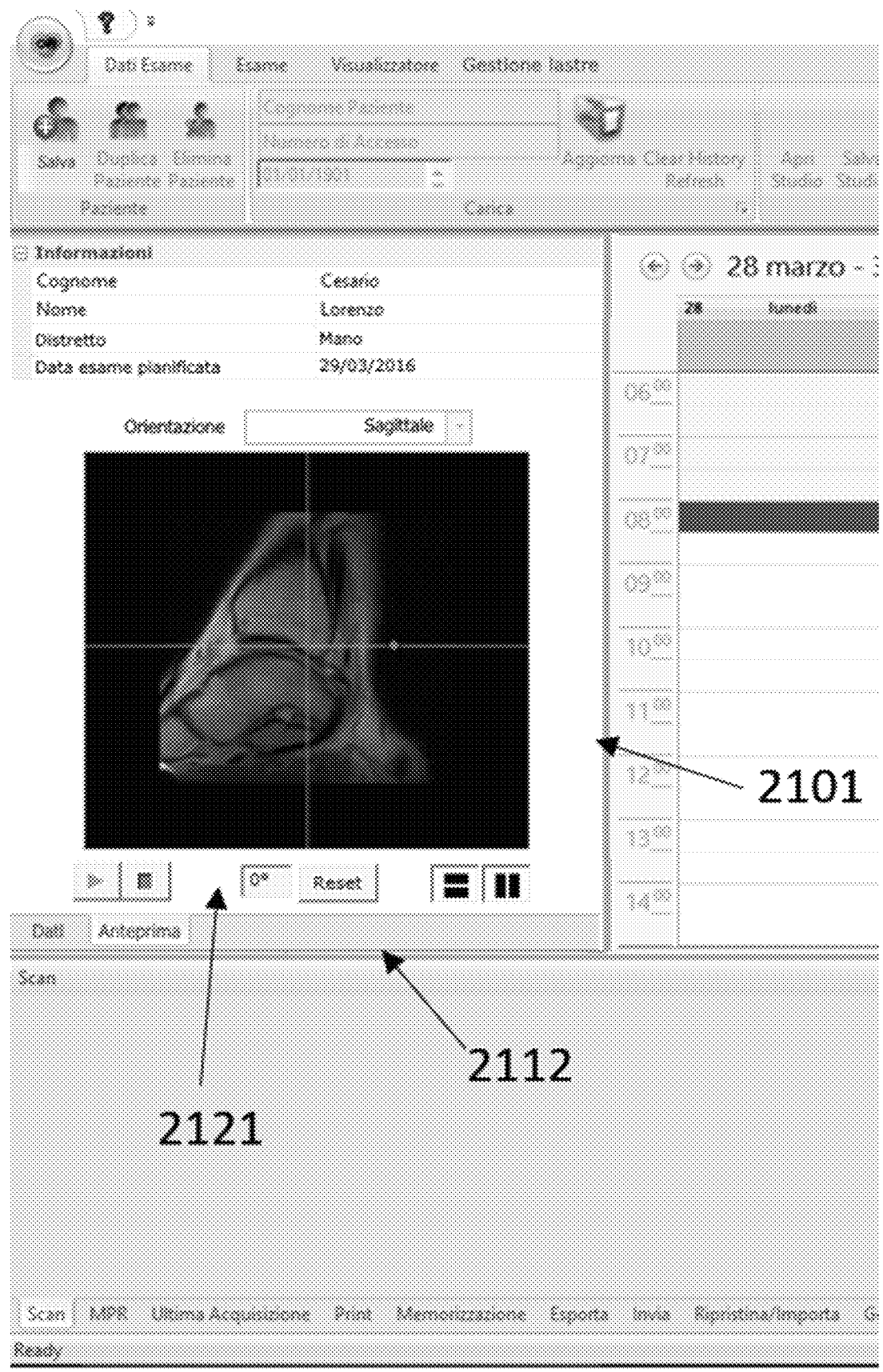
Figure 21B:
Figure 21C:
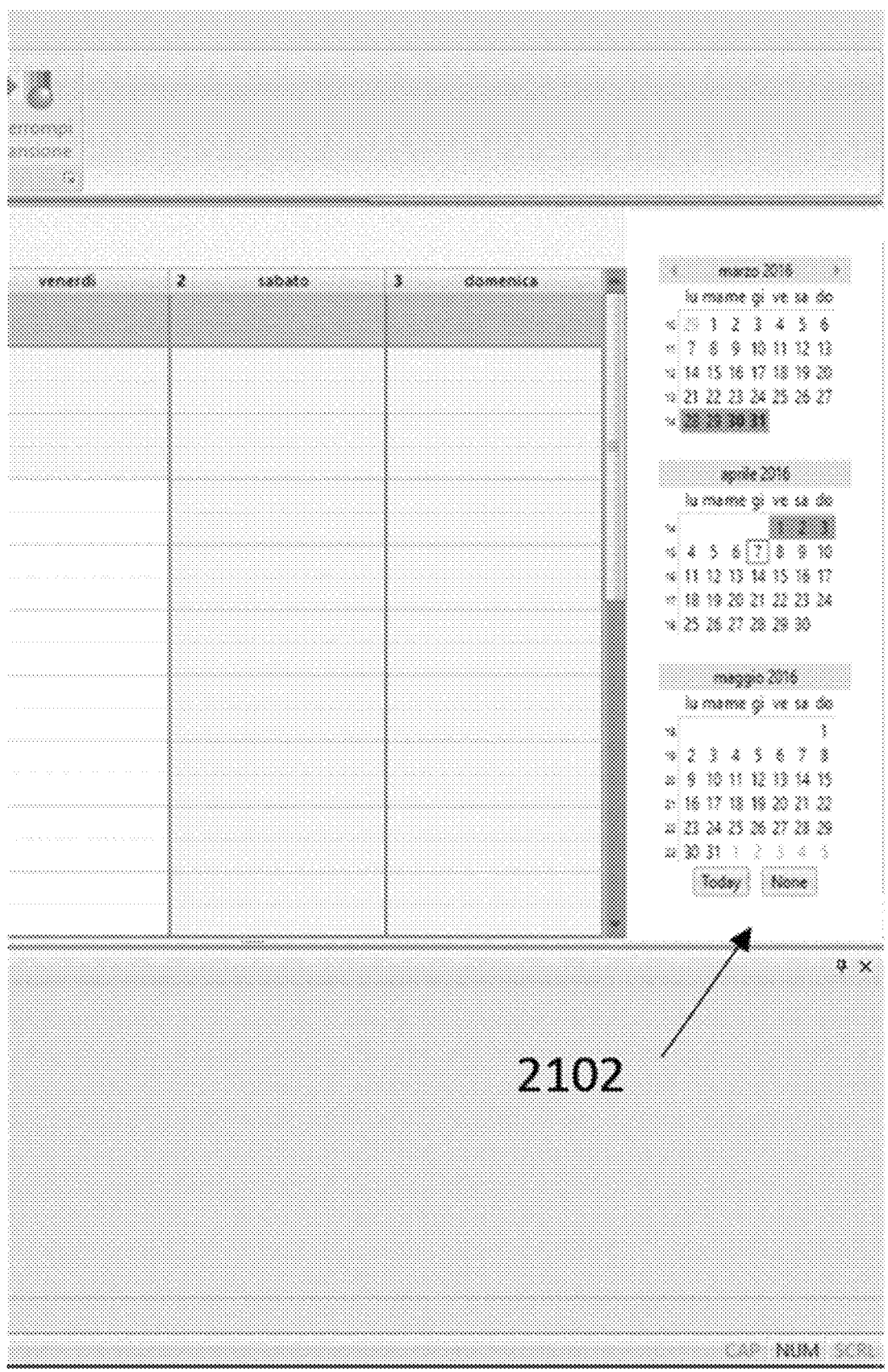

FIGS. 20 and 21 show examples of GUI configuration of the windows relating to an examination scheduling function. The structure of the windows is generated according to the same principles of the preceding examples and the tool bars, the button bars, the groups and the active groups as well as the division of the screen in several different display areas is maintained. The active elements of the GUI are also here contextualized in relation to the task and functions. In the right-hand display area 2002 and 2102 of respectively FIGS. 20 and 21 a condensed monthly calendar representation is shown and on it the days at which activities are to be carried out or have been carried out are highlighted. In the central display field 2000 and 2100 of respectively FIGS. 20 and 21 the expanded week calendar of a selected week is shown and the planned examination as well as the examination carried out are registered and differently highlighted in relation to their status.

In the left display area 2001 of FIG. 20 the patient data of a selected scheduled examination indicated in the example as 2020 in the expanded weekly calendar are shown. In FIG. 21, the right hand display area 2101 which relates to an examination which has already carried out displays the pre-view of the acquired images since in the bar 2112 the label preview is selected differently from the example of FIG. 20 in which in the bar 2012 the label data is selected. The preview can be managed by using active managing buttons on a preview tool bar 2121 which is displayed below the field in which the images of the preview are visualized.

The invention claimed is:

1. An MRI control system with a user interface, wherein the user interface comprises more than one automatically configured window, each window being configured in a pre-set manner to have functions and tools for carrying out a specific task or process;
    the system is configured to display the windows one at a time, in an overlapping manner, or one beside the other,
    the system further including a hardware processor that is configured to automatically:
    select basic operational elements needed to carry out the specific task or process for each window:
    put together the selected basic operational elements in a frame: and
    display the frame for the user:
    the configuration of each window being automatically configured to comprise a task or process contextualized combination of a frame and graphic represented input tool, each of the input tools configured for activating a specific function needed in relation to the specific task or process.

2. An MRI control system according to claim 1 in which at least one of the windows is configured to provide for at least one further area for displaying the dynamic and interactive structure of a database or a file system comprising data records or data files related to patients, the tree structure comprising icons univocally related to the folder and files each icon being an active button for selecting and opening the folder and/or selecting and opening a file contained in a folder and each icon being univocally related to a folder or file path addressing the location of the folder and the file in the database structure and/or in a file system of a memory in which the folder and files are created and stored.

3. An MRI control system according to claim 1, in which comprising a file path manager and tracker carrying out an automatic dynamic interaction between the records in a database and/or data or image files in a file system of a logic memory unit relating to single cases of the same patient or of different patient and address the record of a database or the file path in the file system to which a visualized image or data report belongs by exercising a selection action on the visualized content of the file such as an image or data of a report or by simply opening the file for visualizing the said image or report.

4. An MRI control System according to claim 1 wherein, the control system of an MRI system comprises:
    a memory for storing a database;
    the database comprising records containing data organized according to a database structure;
    the memory being configured according to a file system comprising files and folders organized in a tree structure;
    the data in the database records and the data files or the image files being univocally addressable by a path and a file name indicating the location of the data or of the files in the database structure and/or in the tree representing the file system structure;
    the said file system and/or the structure of the data base being represented by a tree in which each folder is represented by a folder icon and/or name and each file is represented by a file icon and/or name;
    the icons being active buttons which provides access to the representation of the content in a folder in form of further folder and/or files and/or opens a file and/or activate management tasks on the folder and/or the files and/or visualizes the content of each opened file on a display;
    the control system being provided with a path manager and tracker, generating a link between each visualized file and configured to save the file specific path and to address automatically the file location in the representation of the structure of the database and/or in the file system representation to which the visualized file content belongs by carrying out a selection activity such a point and click operation on the area in which the file content is displayed.

5. An MRI control system according to claim 1, in which the database structure and/or the file format and file names are defined according to the DICOM standard.

6. An MRI control system according to claim 1, in which when creating new records comprising new folders, new data and or image or CAD files, the path manager and tracker assigns automatically a path to the said folder and/or file and/or record according to the structure of the database and/or of the file system.

7. An MRI system, wherein the MRI system comprises a control unit with a processor executing a control program configuring the said processor to operate for generating a user interface according to claim 1.

8. An MRI system according to claim 7, wherein the MRI system comprises:
    a cavity for accommodating a target body under examination or a part thereof
    a magnet for generating a static magnetic field in a volume of space;

gradient coils for generating gradient magnetic fields in addition to the static magnetic field according to three spatial directions;

a control unit configured to drive and control the gradient coils and the magnet;

a transmission antenna connected to an excitation signal sequence generator for transmitting spin echo excitations signals into the cavity housing the target body;

a receipt antenna for receiving the MRI signals caused by the excitation signals;

an MRI receipt signals processing unit and image generation unit for processing the signals and extracting image data information and for generating the images;

a display unit for displaying the reconstructed images;

a control system comprising a processor executing a software for configuring the control system to carry out the managing of the image acquisition process, of the image reconstruction process the and/or of the processing of the acquired images and/or the managing of the patient data and the image and data storage process;

the said control system comprising a user interface for input of commands and visualization of data and/or images;

the control system being provided with a data and image files path manager and tracker configured to dynamically link the visualized images or data of a file with the path of said file in a file system and/or in a database structure where the file is saved;

the said user interface being provided with a display area in which the tree structure of the database and/or of the file system is represented comprising icons representing folders and files of the database and/or file system structure and in which the icon of the file is automatically highlighted and selected when the said file is open and the content visualized in foreground in a further display area for the said file content.

9. An MRI system according to claim 7, in which the user interface control program is executed by the control system and configures the said control system for displaying the user interface on the display screen.

10. A method for managing records of a database and/or data and image files with a user interface, the said files being saved in a logical memory location defined by a file system structure and/or in a location in the structure of the database, each file being univocally identified by a file name, a dedicated icon and a path in the file system identifying one or more nested folders in which the file is saved, the said method comprises the steps of displaying in a dedicated area the a tree structure of the file system and/or of the database and highlighting in the said tree structure a file which is open;

displaying the file content in a display area besides the area for displaying the tree structure of the file system or the database structure and in a dedicated window, the dedicated window being one of a plurality of windows, each of the plurality of windows being configured in a pre-set manner for carrying out a specific task or function;

automatically updating the representation of the tree structure of the file system or the representation of the structure of the database when the window showing the content of an open file is shifted in a foreground for visualization or a selection action is executed on the display area in which the file content is displayed by highlighting the file name and icon in the said tree structure corresponding to the file content in the window being visualized in the foreground.

11. A method according to claim 10 in which the step is provided of automatically maintaining or activating the link to the location of storing each currently visualized file in the tree representation of the file system and/or in the structure of the database when the file content of the corresponding file is visualized in the foreground.

12. A method according to claim 10, in which each file is opened in a respective one of the dedicated windows and when several files are opened at the same time the windows are displayed in an overlaid order, the content of each file being alternatively brought the foreground to be seen by the user by a command.

13. A method according to claim 10, in which at least two images are displayed in image windows or display areas which are visualized one beside the other a window or display area being selected by a selection action carried out on it and the representation of the file system and/or of the database structure being updated for highlighting the path and the file related to the selected file content on the selected display area.

14. The MRI control system according to claim 1, wherein the system is configured to display the windows one at a time.

15. The MRI control system according to claim 1, wherein the system is configured to display the windows in an overlapping manner.

16. The MRI control system according to claim 1, wherein the system is configured to display the windows one beside the other.

17. An MRI control system comprising a user interface, the user interface comprising:

one or more automatically configured windows, each of the windows being an interface configured in a pre-set manner to have functions and tools for carrying out a specific task or process;

the control system comprising a hardware processor configured to selectively display the windows alternatively in an overlaid manner or one beside the other, the control system that is configured to automatically:

select basic operational elements needed to carry out the specific task or process for each window:

put together the selected basic operational elements in a frame: and display the frame for the user:

the configuration of each window comprising one of a task or a process in the form of a frame and graphics representing input tools, wherein each of the tools is configured to activate a specific function needed in relation to the specific tasks or processes.

18. The MRI control system according to claim 17, wherein the system is configured to display the windows in an overlapping manner.

19. The MRI control system according to claim 17, wherein the system is configured to display the windows one beside the other.

20. The MRI control system according to claim 17, wherein the hardware processor is configured to automatically:

select basic operational elements needed to carry out the specific task or process for each window;

put together the selected basic operational elements in a frame; and display the frame for the user.

21. An MRI control system with a user interface, wherein the user interface comprises more than one automatically configured window, each window being configured in a pre-set manner to have functions and tools for carrying out a specific task or process;

the system is configured to display the windows one at a time, in an overlapping manner, or one beside the other, the configuration of each window being automatically configured to comprise a task or process contextualized combination of a frame and graphic represented input tools, each of the input tools configured for activating a specific function needed in relation to the specific task or process;

wherein the system of an MRI system comprises:

a memory for storing a database;

the database comprising records containing data organized according to a database structure;

the memory being configured according to a file system comprising files and folders organized in a tree structure;

data in the database records, data files or image files being univocally addressable by a path and a file name indicating the location of the data or of the files in the database structure and/or in the tree representing the file system structure;

the file system and/or the structure of the data base being represented by a tree in which each folder is represented by a folder icon and/or name and each file is represented by a file icon and/or name;

the icons being active buttons which provide access to the representation of the content in a folder in form of a further folder and/or files and/or opens a file and/or activates management tasks on the folder and/or the files and/or visualizes the content of each opened file on a display;

the control system being provided with a path manager and tracker configured to generate a link between each visualized file and configured to save a file specific path and to address automatically the file location in the representation of the structure of the database and/or in the file system representation to which the visualized file content belongs by carrying out a selection activity such a point and click operation on the area in which the file content is displayed.

\* \* \* \* \*